(12) United States Patent
Moshe et al.

(10) Patent No.: US 6,463,794 B1
(45) Date of Patent: Oct. 15, 2002

(54) METHOD AND DEVICE FOR NON-INVASIVELY DETERMINING MOISTURE CONTENT AND UNIFORMITY OF SOLID PLANT MATTER DURING ON-LINE DRYING OR COOLING FORCED-AIR TREATMENT

(75) Inventors: Danny S. Moshe, Kiryat Ono (IL); Alexander Greenwald, Nazirith Illit (IL); Nikolay Tsypto, Nazirith Illit (IL)

(73) Assignees: Malcam Ltd., Tel Aviv (IL); AM Vision Technologies Ltd., Tel Aviv (IL)

( * ) Notice: Subject to any disclaimer, the term of this patent is extended or adjusted under 35 U.S.C. 154(b) by 0 days.

(21) Appl. No.: 09/546,383

(22) Filed: Apr. 10, 2000

(51) Int. Cl.[7] ............................................. G01N 25/56
(52) U.S. Cl. ............................................................ 73/73
(58) Field of Search ............................................... 73/73

(56) References Cited

U.S. PATENT DOCUMENTS

| | | | |
|---|---|---|---|
| 4,263,720 A | * 4/1981 | Bowling | 34/22 |
| 4,580,233 A | * 4/1986 | Parker et al. | |
| 4,788,853 A | * 12/1988 | Bell | 73/73 |
| 5,038,498 A | 8/1991 | Woolsey | 34/225 |
| 5,163,454 A | * 11/1992 | Clemons | 131/302 |
| 5,845,529 A | 12/1998 | Moshe et al. | 324/640 |
| 5,870,926 A | 2/1999 | Saito et al. | 73/73 |
| 6,025,724 A | 2/2000 | Moshe et al. | 73/73 |
| 6,068,874 A | * 5/2000 | Grocholski | 426/465 |
| 6,107,809 A | * 8/2000 | Moshe et al. | |

* cited by examiner

*Primary Examiner*—Hezron Williams
*Assistant Examiner*—Rodney Frank
(74) *Attorney, Agent, or Firm*—G. E. Ehrlich Ltd.

(57) ABSTRACT

Method and device for non-invasively determining moisture content and uniformity of solid plant matter during on-line drying or cooling forced-air treatment featuring measuring primary operating parameters of temperature, humidity, and flow rate of forced-air entering and exiting the volume of solid plant matter moving through an on-line drying or cooling forced-air treatment device. Empirically determined data relating the influence of secondary operating parameters of volumetric bulk material transport rate of the solid plant matter, type of the solid plant matter, and physico-chemical characteristics and properties of the solid plant matter, on the sensing and measuring of the primary forced-air operating parameters are used for process correcting raw temperature, humidity, and flow rate, parametric values of the forced-air entering and exiting the solid plant matter, leading to the determination of highly accurate and reproducible values of moisture content and uniformity of the solid plant matter. Moisture content and uniformity values correspond to the volume of the solid plant matter.

123 Claims, 1 Drawing Sheet

METHOD AND DEVICE FOR NON-INVASIVELY DETERMINING MOISTURE CONTENT AND UNIFORMITY OF SOLID PLANT MATTER DURING ON-LINE DRYING OR COOLING FORCED-AIR TREATMENT

FIELD AND BACKGROUND OF THE INVENTION

The present invention relates to determining moisture content and uniformity of solid plant matter, and more particularly, to a method for non-invasively determining moisture content and uniformity of solid plant matter during on-line drying or cooling forced-air treatment, based on measuring temperature, humidity, and flow rate of the forced-air passing through the volume of the solid plant matter.

A wide variety of raw materials used for manufacturing food, pharmaceutical, and tobacco products are obtained from solid plant matter. Hereinafter, the term 'solid plant matter' refers to any essentially solid part or component of a plant, including, but not limited to, leaves, beans, seeds, grains, flowers, stems, stalks, and roots, in raw or processed, loose or web, form. For example, tea leaves, coffee beans, and tobacco leaves are used for manufacturing tea, coffee, and tobacco products, respectively.

From the site of cultivation, raw solid plant matter is harvested, bundled or packaged, transported, and stored in a variety of forms before being used in manufacturing processes. Subsequent food, pharmaceutical, and tobacco product manufacturing processes are performed in stages involving a variety of procedures, from initial processing of loose raw solid plant matter leading to using the initially processed solid plant matter for producing bulk quantities of various consumer end products. These end products are subsequently sub-divided, packaged, stored, and transported throughout the consumer marketplace according to distribution, marketing, and selling criteria.

The present invention focuses on that stage of the manufacturing sequence involving in-house treatment of initially processed raw solid plant matter. In particular, the stage involving drying or cooling of wetted raw solid plant matter by subjecting it to an on-line forced-air treatment. As part of an overall manufacturing sequence, some types of raw solid plant matter are intentionally and controllably wetted, for example, by subjecting them to steam, for the purpose of enhancing particular physicochemical properties of the raw solid plant matter needed for entry into further downstream processes. For example, raw tobacco leaves are wetted for causing opening of pores of the leaves, resulting in enhancing particular physicochemical properties of the tobacco leaves essential to characteristics and performance of tobacco end products.

In such a manufacturing sequence, wetted raw solid plant matter exiting a wetting apparatus is transported by an on-line conveyor passing through a drying or cooling apparatus, such as a multiple open sided chamber, featuring an inlet and outlet through which forced-air passes, thereby drying or cooling the wetted solid plant matter. During the drying or cooling forced-air treatment, moisture content, and consequently, uniformity, throughout the volume of the initially wetted solid plant matter change, according to the operating parameters of the forced-air treatment. At this stage of such a manufacturing sequence, moisture content and uniformity are important properties of the solid plant matter which need to be determined, monitored, and controlled prior to the solid plant matter entering further downstream processes or storage. In particular, if the moisture content and/or uniformity of a given wetted solid plant matter raw material are outside of established quality control values, use of such solid plant matter is expected to lead to downstream intermediate products, or stored solid plant matter, similarly failing their established quality control values, potentially causing undesirable rejection of material, manufacturing down time and added cost.

Recently, several methods and devices, based on microwave technology, have been disclosed for on-line non-invasively measuring and calculating moisture content of materials, including plant derived materials such as cotton, tea leaves, and tobacco leaves. Disclosures include U.S. patent application Ser. Nos. 09/143,966; 09/126,384; 08/974,983, and 08/777,872. In these disclosures, typically, a radiation source beam is transmitted through a portion of material and is received by a receiving antenna, which then produces a signal. Microwave signal parameters such as attenuation and phase shift are used to measure and determine moisture content, density, and uniformity of the material. The disclosed methods and devices are primarily applicable to bulk quantities of loose or packaged materials, such as bales, being transported on-line through a silo or being transported between bulk material storage facilities, and include no description relating to measuring or determining moisture content of the material during a drying or cooling process.

In U.S. Pat. No. 5,870,926, there is teaching of applying infrared spectroscopy for non-invasively determining moisture content of solid plant matter during an on-line drying or cooling treatment. In this disclosure, exposed surface area of solid plant matter passing through a drying or cooling apparatus is subjected to an infrared beam, whose output is compared to the output of a reference or calibration beam, for obtaining on-line values of infrared reflections proportional to moisture content of the solid plant matter exiting the drying or cooling apparatus. In practice, the disclosed method and device are significantly limited by interference during the infrared measurements, caused by the presence of varying quantities of dirt on the surface of the infrared source and receiver apparatus, and dust in the surrounding air. This disclosure is additionally limited by the infrared measurements providing information relating only to the exposed surface area of the solid plant matter during on-line transport, and is not capable of providing moisture content or uniformity information relating to the volume of the moving solid plant matter. Even for low density loose solid plant matter, results of moisture content or uniformity obtained by related methods and devices are significantly limited.

Aside from radiation based methods and devices, currently available methods and devices for non-invasively determining moisture content, and consequently, uniformity, of wetted solid plant matter passing through an on-line drying or cooling forced-air treatment are typically based on only measuring the humidity of the forced-air passing through the drying or cooling device. Here, for a given temperature, the difference in humidity of the forced-air entering and exiting the drying or cooling apparatus is proportional to moisture content, and consequently, uniformity, of the solid plant matter exiting the drying or cooling apparatus.

Actually, in an on-line drying or cooling forced-air treatment of wetted solid plant matter, measurement of several operating parameters, in addition to humidity of the forced-air, is required for accurately and reliably determining moisture content and uniformity of the continuously moving solid plant matter. Primary operating parameters most affecting moisture content and uniformity of the moving solid plant matter are the temperature, humidity, and flow rate of the forced-air used for drying or cooling the wetted solid plant matter as it passes through a drying or cooling apparatus. Secondary operating parameters affecting moisture content and uniformity of the moving solid plant matter include (1) the volumetric bulk material transport rate of the solid plant matter transported by an on-line conveyor through the drying or cooling apparatus during the drying or cooling forced-air treatment, where this operating parameter is a function of the configuration or volume of the bulk solid plant matter fed onto, and situated on, the on-line conveyor, and a function of the linear speed or velocity of the on-line conveyor, (2) the type of solid plant matter, as described above, and (3) physicochemical characteristics and properties, such as density, of the solid plant matter subjected to the on-line drying or cooling forced-air treatment.

To one of ordinary skill in the art, there is thus a need for, and it would be useful to have a method and device for non-invasively determining moisture content and uniformity of solid plant matter during on-line drying or cooling forced-air treatment, based on measuring temperature, humidity, and flow rate of the forced-air passing through the volume of the solid plant matter. Moreover, accurate and precise determination of moisture content and uniformity of solid plant matter during forced-air treatment would enable optimization and control of the drying or cooling forced-air treatment, thereby contributing to optimization and control of an overall manufacturing sequence for producing consumer end products containing solid plant matter raw materials.

SUMMARY OF THE INVENTION

The present invention relates to a method and device for non-invasively determining moisture content and uniformity of solid plant matter during on-line drying or cooling forced-air treatment, based on measuring multiple operating parameters including temperature, humidity, and flow rate of the forced-air passing through the volume of the moving solid plant matter.

It is therefore an object of the present invention to provide a method and device for non-invasively determining moisture content and uniformity of solid plant matter during on-line drying or cooling forced-air treatment.

It is a further object of the present invention to provide such a method and device which are based on measuring primary operating parameters of temperature, humidity, and flow rate of the forced-air passing through the volume of the solid plant matter.

It is another object of the present invention to provide such a method and device which are also based on using empirically determined measurements and data featuring secondary operating parameters of volumetric bulk material transport rate of the solid plant matter, type of the solid plant matter, and physicochemical characteristics and properties of the solid plant matter, for process correcting raw parametric values of temperature, humidity, and flow rate, of the forced-air entering and exiting the volume of the solid plant matter.

Thus, according to the present invention, there is provided a method for non-invasively determining moisture content and uniformity of solid plant matter during on-line drying or cooling forced-air treatment, comprising the steps of: (a) sensing and measuring forced-air operating parameters while forced-air enters and exits the solid plant matter, said forced-air operating parameters include temperature, humidity, and flow rate; (b) processing said forced-air operating parameters for forming forced-air parametric values, said forced-air parametric values include forced-air temperature values, forced-air humidity values, and forced-air flow rate values; (c) calculating a moisture content value of the solid plant matter from said forced-air parametric values; and (d) calculating a uniformity value of the solid plant matter from at least two said moisture content values of the solid plant matter.

According to another aspect of the present invention, there is provided a method for non-invasively determining moisture content and uniformity of solid plant matter during on-line drying or cooling forced-air treatment, comprising the steps of: (a) sensing and measuring at least one set of inlet forced-air operating parameters and at least one set of outlet forced-air operating parameters, while forced-air enters and exits the solid plant matter, each said set of said forced-air operating parameters includes temperature, humidity, and flow rate; (b) processing each said set of inlet forced-air operating parameters and each set of outlet forced-air operating parameters, for forming at least one set of inlet forced-air parametric values and at least one set of outlet forced-air parametric values; (c) calculating a moisture content value of the solid plant matter from each said set of inlet forced-air parametric values and each said set of outlet forced-air parametric values; and (d) calculating a uniformity value of the solid plant matter from at least two said moisture content values of the solid plant matter.

According to another aspect of the present invention, there is provided a method for non-invasively determining moisture content and uniformity of solid plant matter during on-line drying or cooling forced-air treatment, comprising the steps of: (a) sensing and measuring forced-air operating parameters while forced-air enters and exits the solid plant matter, said forced-air operating parameters include temperature, humidity, and flow rate; (b) generating raw forced-air parametric values from said sensed and measured forced-air operating parameters, said raw forced-air parametric values include raw forced-air temperature values, raw forced-air humidity values, and raw forced-air flow rate values; (c) process correcting said generated forced-air parametric values for forming process corrected forced-air parametric values, said process corrected forced-air parametric values include process corrected forced-air temperature values, process corrected forced-air humidity values, and process corrected forced-air flow rate values, said process correcting accounts for affects of at least one secondary operating parameter on the step of said sensing and measuring said forced-air operating parameters of temperature, humidity, and flow rate; (d) calculating a moisture content value of the solid plant matter from said process corrected forced-air parametric values; and (e) calculating a uniformity value of the solid plant matter from at least two said moisture content values of the solid plant matter.

According to another aspect of the present invention, there is provided a method for non-invasively determining moisture content and uniformity of solid plant matter during on-line drying or cooling forced-air treatment, comprising the steps of: (a) sensing and measuring forced-air operating parameters while forced-air enters and exits the solid plant matter, said forced-air operating parameters include temperature, humidity, and flow rate; (b) generating raw forced-air parametric values from said sensed and measured forced-air operating parameters, said raw forced-air parametric values include raw forced-air temperature values, raw forced-air humidity values, and raw forced-air flow rate values; (c) process correcting said generated forced-air parametric values for forming process corrected forced-air parametric values, said process corrected forced-air parametric values include process corrected forced-air temperature values, process corrected forced-air humidity values, and process corrected forced-air flow rate values, said process correcting accounts for affects of at least one secondary operating parameter on the step of said sensing and measuring said forced-air operating parameters of temperature, humidity, and flow rate; (d) calculating a moisture content value of the solid plant matter from said process corrected forced-air parametric values; and (e) calculating a uniformity value of the solid plant matter from at least two said moisture content values of the solid plant matter.

The method and device of the present invention serve as significant improvements over currently used methods and devices for determining moisture content and uniformity of solid plant matter during on-line drying or cooling forced-air treatments, by providing values of moisture content and uniformity corresponding to the entire volume of moving solid plant matter, based on accurately and reproducibly measuring and using primary and secondary operating parameters during the drying or cooling forced-air treatment. This leads to achieving high levels of optimization and control of the drying or cooling forced-air treatment, thereby contributing to optimization and control of an overall manufacturing sequence for producing consumer end products containing solid plant matter raw materials.

BRIEF DESCRIPTION OF THE DRAWING

The invention is herein described, by way of example only, with reference to the accompanying drawing, wherein.

DESCRIPTION OF THE PREFERRED EMBODIMENTS

Figure 1:
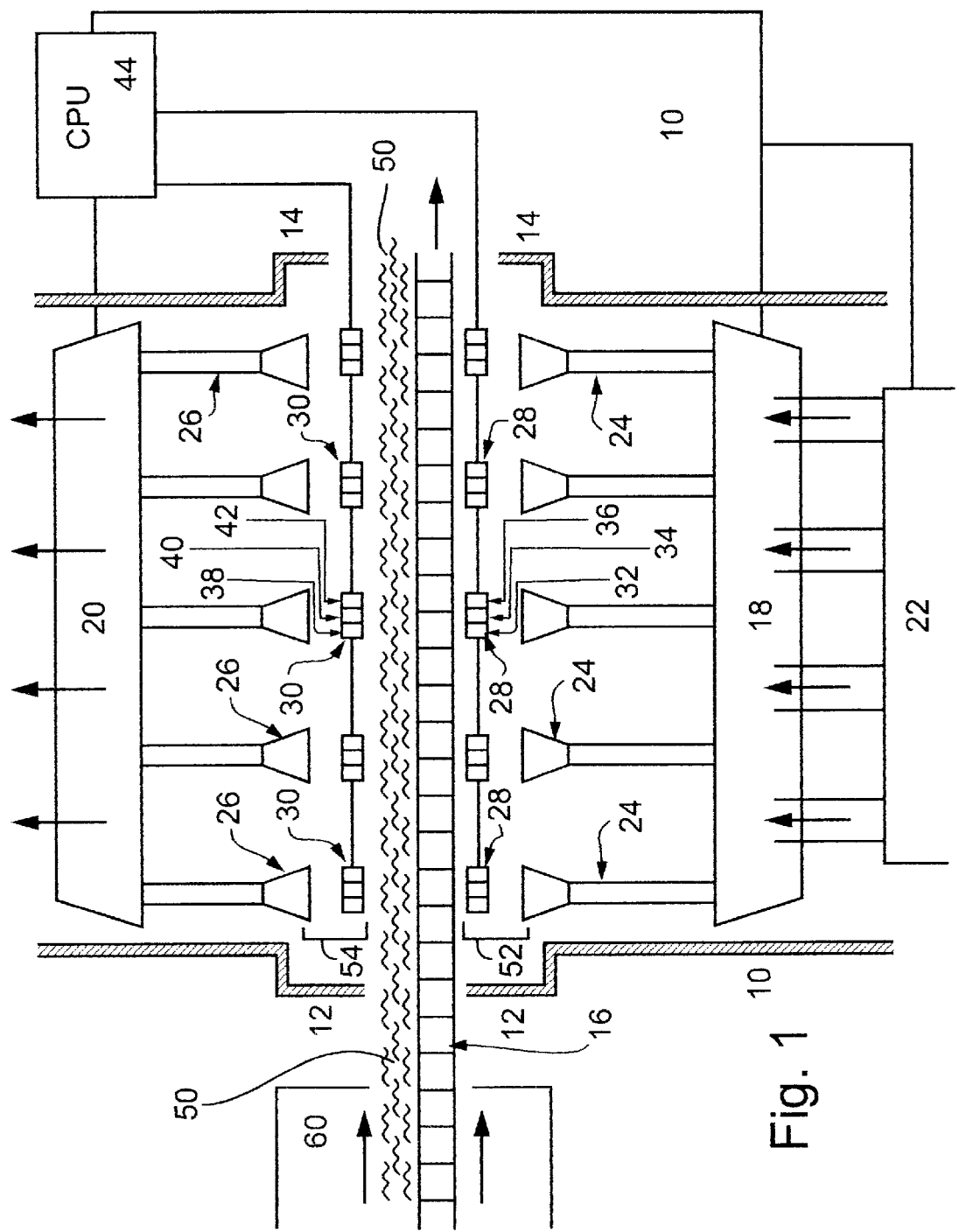
FIG. 1 is a schematic diagram illustrating an exemplary preferred embodiment of the device for non-invasively determining moisture content and uniformity of solid plant matter during on-line drying or cooling forced-air treatment, in accordance with the present invention.

The present invention is of a unique method and device for non-invasively determining moisture content and uniformity of solid plant matter during on-line drying or cooling forced-air treatment.

The method and device of the present invention feature measuring primary operating parameters of temperature, humidity, and flow rate of the forced-air entering and exiting the volume of moving solid plant matter during the on-line drying or cooling forced-air treatment, and using these measurements and empirically determined data featuring secondary operating parameters for highly accurately and reproducibly calculating moisture content and uniformity of the moving solid plant matter during the forced-air treatment.

Empirically determined data relating the influence of secondary operating parameters of volumetric bulk material transport rate of the solid plant matter, type of the solid plant matter, and physicochemical characteristics and properties of the solid plant matter, on the step of sensing and measuring the primary forced-air operating parameters of temperature, humidity, and flow rate, are used for process correcting raw parametric values of temperature, humidity, and flow rate, of the forced-air entering and exiting the solid plant matter, which are subsequently used for determining highly accurate and reproducible values of moisture content and uniformity of the solid plant matter. Moisture content and uniformity values thus obtained correspond to the volume of the moving solid plant matter, and are not limited to the exposed surface of the moving solid plant matter, as taught in the prior art.

It is to be understood that the invention is not limited in its application to the details of construction, arrangement, and composition of the components set forth in the following description and accompanying drawing. The following description refers to an exemplary device used in a drying or cooling forced-air treatment of solid plant matter, in order to illustrate implementation of the present invention. The invention is capable of other embodiments or of being practiced or carried out in various ways. Also, it is to be understood that the phraseology and terminology employed herein are for the purpose of description and should not be regarded as limiting.

Components and operation of the preferred embodiment of the device used for implementing the method of the present invention are herein described. Steps and sub-steps of the preferred embodiment of the method for non-invasively determining moisture content and uniformity of solid plant matter during on-line drying or cooling forced-air treatment, according to the present invention are described thereafter.

Referring now to the drawings, FIG. 1 illustrates an exemplary preferred embodiment of the device for implementing the method of the present invention. Device 10 is designed for subjecting solid plant matter 50 to the on-line drying or cooling forced-air treatment. Device 10 features (i) a solid plant matter inlet 12, (ii) a solid plant matter outlet 14, and (iii) a solid plant matter transport mechanism 16, such as a conveyor, for on-line automatically and controllably, continuously or discontinuously, transporting solid plant matter 50 into and out of the device. Device 10 also features (iv) a forced-air inlet unit 18, (v) a forced-air outlet unit 20, and (vi) a forced-air supply mechanism 22 for on-line automatically and controllably, continuously or discontinuously, forcing an air supply into and out of device 10 and the volume of solid plant matter 50.

In a typical manufacturing scenario, steamed or wetted solid plant matter 50 leaves a steaming, wetting, or humidifying apparatus 60 and enters solid plant matter inlet 12 of device 10 for drying or cooling forced-air treatment. The volumetric bulk material transport rate of the solid plant matter transported by an on-line conveyor through the drying or cooling apparatus during the drying or cooling forced-air treatment is set according to the configuration or volume of the bulk solid plant matter fed onto, and situated on, solid plant matter transport mechanism 16, such as an on-line conveyor, and of the linear speed or velocity of solid plant matter transport mechanism 16.

Forced-air inlet unit 18 features a single forced-air inlet element 24, or features a plurality of forced-air inlet elements 24, for guiding the forced-air into solid plant matter 50. Similarly, forced-air outlet unit 20 features a single forced-air outlet element 26, or features a plurality of forced-air outlet elements 26, for guiding the forced-air out of solid plant matter 50. Forced-air inlet unit 18 and force-air outlet unit 20 may each be fixed in place in device 10, or may each be mobile for movement through device 10. Moreover, any number of forced-air inlet elements 24 and/or any number of forced-air outlet elements 26 may be fixed in place in device 10, or may be mobile for movement through device 10.

Forced-air supply mechanism 22 is capable of supplying forced-air having conditions of laminar or turbulent flow, to the moving solid plant matter 50, for example, by varying operating parameters or properties of the forced-air, such as temperature, pressure, volumetric flow rate, density, and viscosity. In particular, the speed by which the method of the present invention determines moisture content and uniformity of solid plant matter 50 is, in part, influenced by the operating parameters and flow characteristics of the forced-air passing through solid plant matter 50, such as whether the forced-air flow is laminar or turbulent.

Device 10 also features (vii) at least one set 28 of, preferably, but not limited to, three, inlet forced-air parametric sensors 32, 34, and 36, and (viii) at least one set 30 of, preferably, but not limited to, three, outlet forced-air parametric sensors 38, 40, and 42, for enabling sensing and measuring operating parameters of the forced-air entering and exiting, respectively, solid plant matter 50 moving through device 10. Preferably, device 10 features a plurality of identical sets 28 of inlet forced-air parametric sensors 32, 34, and 36, and a plurality of identical sets 30 of outlet forced-air parametric sensors 38, 40, and 42. Any number of the at least one set 28 of inlet forced-air parametric sensors and/or any number of the at least one set 30 of outlet forced-air parametric sensors may be fixed in place in device 10, or may be mobile for movement through device 10. Moreover, any number of inlet forced-air parametric sensors 32, 34, and 36, and/or any number of outlet forced-air parametric sensors 38, 40, and 42, may be fixed in place in device 10, or may be mobile for movement through device 10.

In this particular embodiment of the method, primary operating parameters of the forced-air entering and exiting the solid plant matter, to be sensed and measured, are temperature, T(air), humidity, H(air), and flow rate, FR(air). In principle, any number of other operating parameters or properties of the forced-air used for drying or cooling the solid plant matter, which can be sensed and measured, can be included in each of the sets 28 and 30 of inlet and outlet forced-air parametric sensors.

The forced-air parametric sensors are devices, mechanisms, or components, preferably of electromechanical design and operation, enabling on-line automatic and controllable, continuous or discontinuous, sensing and measuring the forced-air operating parameters of temperature, humidity, and flow rate, as the forced-air enters and exits the moving solid plant matter 50.

Accordingly, each set 28 of inlet forced-air parametric sensors includes (1) an inlet forced-air temperature sensor 32, for sensing and measuring the inlet forced-air temperature, $T_{in}$(air), (2) an inlet forced-air humidity sensor 34, for sensing and measuring the inlet forced-air humidity, $H_{in}$(air), and (3) an inlet forced-air flow rate sensor 36, for sensing and measuring the inlet forced-air flow rate, $F_{in}$(air). Each set 30 of outlet air parametric sensors includes (1) an outlet forced-air temperature sensor 38, for sensing and measuring the outlet forced-air temperature, $T_{out}$(air), (2) an outlet forced-air humidity sensor 40, for sensing and measuring the outlet forced-air humidity, $H_{out}$(air), and (3) an outlet forced-air flow rate sensor 42, for sensing and measuring the outlet forced-air flow rate, $FR_{out}$(air).

According to actual design and resulting geometrical and spatial configuration, of device 10 and device components used for drying or cooling forced-air treatment of solid plant matter 50, there are different particular ways of device 10 featuring the at least one set 28 of inlet forced-air parametric sensors, and the at least one set 30 of outlet forced-air parametric sensors. Specifically, according to electromechanical design, and resulting geometrical and spatial positioning and alignment, of forced-air inlet unit 18, forced-air inlet elements 24, and inlet forced-air parametric sensors 32, 34, and 36, relative to forced-air outlet unit 20, forced-air outlet elements 26, and outlet forced-air parametric sensors 38, 40, and 42.

Preferably, forced-air inlet unit 18 and forced-air outlet unit 20 are electro-mechanically configured such that, each forced-air inlet element 24 is associated, and axially aligned, with a localized set 28 of inlet forced-air parametric sensors 32, 34, and 36, and, each forced-air outlet element 26 is associated, and axially aligned, with a localized set 30 of outlet forced-air parametric sensors 38, 40, and 42. More preferably, each association, where an exemplary single inlet association is referenced as 52, of forced-air inlet element 24 and localized set 28 of inlet forced-air parametric sensors is electro-mechanically paired, and axially aligned, with a corresponding association, where an exemplary single outlet association is referenced as 54, of forced-air outlet element 26 and localized set 30 of outlet forced-air parametric sensors. This type of electro-mechanical configuration enables obtaining and spatially pairing a set of sensed and measured inlet forced-air parameters with a corresponding set of sensed and measured outlet forced-air parameters, in the same local vicinity of the forced-air entering and exiting, respectively, solid plant matter 50 moving through device 10.

Device 10 further features (ix) a central processing unit 44, and (x) a plurality of control/data links (shown without reference numbers) among device components.

Central processing unit 44 is for automatically and controllably operating device 10 and device components. This includes sending control/data signals to device components, receiving data signals from device components, and, processing and storing data signals and data received from device components. In particular, this includes operating solid plant matter transport mechanism 16, for example, by controlling the quantity, in terms of mass, volume, or density, and/or rate of solid plant matter 50 passing through device 10, such as by controlling a conveyor linear speed or velocity. This also includes operating forced-air inlet unit 18 and forced-air outlet unit 20, and forced-air supply mechanism 22, for example, by controlling the quantity, rate, and/or parameters, of the forced-air passing through solid plant matter 50, such as by opening or closing selected forced-air inlet elements 24 and/or forced-air outlet elements 26, and controlling, for example, temperature, pressure, humidity, and/or flow rate of the forced-air supplied by forced-air supply mechanism 22.

Central processing unit 44 also enables determining values of moisture content and uniformity of the solid plant matter, by converting, storing, processing, and performing calculations on, data received from inlet sets 28 and outlet sets 30 of forced-air parametric sensors 32, 34, and 36, and, 38, 40, and 42, respectively, during the forced-air treatment.

Central processing unit 44 is also used for obtaining, processing, and storing calibration and process related empirical data. Calibration and process related empirical data features, for example, determinations of moisture content and uniformity made during conditions involving well characterized and controlled primary operating parameters of forced-air temperature, humidity, and flow rate, and, well characterized and controlled secondary operating parameters of (1) the volumetric bulk transport rate of solid plant matter 50 transported by solid plant matter transport mechanism 16, such as a conveyor, through drying or cooling device 10 during the on-line drying or cooling forced-air treatment, where this operating parameter is a function of the configuration or volume of the bulk solid plant matter 50 fed onto, and situated on, solid plant matter transport mechanism 16, and a function of the linear speed or velocity of solid plant matter transport mechanism 16, (2) the type of solid plant matter 50, and (3) physicochemical characteristics and properties, including known moisture content and uniformity, of solid plant matter 50 subjected to the drying or cooling forced-air treatment. Calibration and process related empirical data are used for process correcting raw inlet and outlet forced-air parametric values. Process corrected inlet and outlet forced-air parametric values are subsequently used for determining values of moisture content and uniformity of solid plant matter 50.

The plurality of control/data links (shown without reference numbers) is for enabling on-line automatic and controllable, continuous or discontinuous, electronic communication between each component of device 10 and central processing unit 44.

Steps and sub-steps of the preferred embodiment of the method for non-invasively determining moisture content and uniformity of solid plant matter during on-line drying or cooling forced-air treatment, according to the present invention are herein described, with reference to FIG. 1.

In Step 1, there is sensing and measuring (i) the at least one set of inlet forced-air operating parameters by the at least one set 28 of inlet forced-air parametric sensors 32, 34, and 36, for generating at least one corresponding set of inlet forced-air parametric sensor electrical signals, and, sensing and measuring (ii) the at least one set of outlet forced-air operating parameters by the at least one set 30 of outlet forced-air parametric sensors 38, 40, and 42, for generating at least one corresponding set of outlet forced-air parametric sensor electrical signals, while the forced-air continuously or discontinuously enters and exits device 10 and the volume of solid plant matter 50 and, while solid plant matter 50 continuously or discontinuously enters and exits device 10.

Preferably, there is simultaneously sensing and measuring each inlet forced-air operating parameter of each set of inlet forced-air operating parameters simultaneously to sensing and measuring each outlet forced-air operating parameter of each paired set of outlet forced-air operating parameters, by electro-mechanically paired and axially aligned sets 28 and 30 of inlet and outlet forced-air parametric sensors, respectively, according to operation of the electro-mechanically paired and axially aligned forced-air inlet and outlet elements 24 and 26, respectively, as described above and illustrated by 52 and 54.

Each forced-air parametric sensor 32–42 senses and measures one of the forced-air operating parameters, T(air), H(air), or FR(air), whereby each forced-air parameter affects an electro-mechanical mechanism of the respective forced-air parametric sensor 32–42, for generating an electrical output signal, such as a voltage or current output signal, where the magnitude of the electrical output signal is functionally proportional to the magnitude of the respective forced-air operating parameter.

Accordingly, each set of inlet forced-air parametric sensor electrical signals includes (1) an inlet forced-air temperature sensor electrical signal, $(S_T)_{in}$, (2) an inlet forced-air humidity sensor electrical signal, $(S_H)_{in}$, and (3) an inlet forced-air flow rate sensor electrical signal, $(S_{FR})_{in}$. Each set of outlet forced-air parametric sensor electrical signals includes (1) an outlet forced-air temperature sensor electrical signal, $(S_T)_{out}$, (2) an outlet forced-air humidity sensor electrical signal, $(S_H)_{out}$, and (3) an outlet forced-air flow rate sensor electrical signal, $(S_{FR})_{out}$.

Step 1 preferably includes sending (i) each of the at least one set of inlet forced-air parametric sensor electrical signals, and (ii) each of the at least one set of outlet forced-air parametric sensor electrical signals, to central processing unit 44.

Preferably, there is simultaneously sending each set of the inlet forced-air parametric sensor electrical signals simultaneously to sending a paired set of the outlet forced-air parametric electrical signals, to central processing unit 44, according to operation of the electro-mechanically paired and axially aligned inlet and outlet forced-air elements 24 and 26, and corresponding sets 28 and 30 of inlet and forced-air outlet parametric sensors 32–42, respectively, as described above and illustratively shown by 52 and 54.

In Step 2, there is also converting (i) each inlet forced-air parametric sensor electrical signal of each of the at least one set of the inlet forced-air parametric sensor electrical signals, and, converting (ii) each outlet forced-air parametric sensor electrical signal of each of the at least one set of the outlet forced-air parametric sensor electrical signals, into a raw, or non-process corrected, value having magnitude and units appropriate for calculating moisture content and uniformity of solid plant matter 50 passing through device 10, by central processing unit 44.

In particular, according to a functional relationship between each sensed and measured inlet forced-air parameter and the corresponding resulting inlet forced-air parametric sensor electrical signal, inlet forced-air parametric sensor electrical signals are converted into appropriate raw inlet forced-air parametric values as follows: $T_{in}(air)^{raw}=F_1[(S_T)_{in}]$, $H_{in}(air)^{raw}=F_2[(S_H)_{in}]$, and $FR_{in}(air)^{raw}=F_3[(S_{FR})_{in}]$, where $F_1$ is a linear or non-linear function of inlet forced-air temperature sensor electrical signal, $(S_T)_{in}$, $F_2$ is a linear or non-linear function of inlet forced-air humidity sensor electrical signal, $(S_H)_{in}$, and, $F_3$ is a linear or non-linear function of inlet forced-air flow rate sensor electrical signal, $(S_{FR})_{in}$, respectively. Moreover, each of the inlet forced-air parametric functions, $F_1[(S_T)_{in}]$, $F_2[(S_H)_{in}]$, and $F_3[(S_{FR})_{in}]$, may also be a linear or non-linear function of any combination of the raw inlet forced-air parametric values, $T_{in}(air)^{raw}$, $H_{in}(air)^{raw}$, and $FR_{in}(air)^{raw}$. Raw Inlet forced-air parametric values are determined at inlet conditions of the forced-air entering the volume of solid plant matter 50 via inlet forced-air elements 24.

Similarly, according to a functional relationship between each sensed and measured outlet forced-air parameter and the corresponding resulting outlet forced-air parametric sensor electrical signal, outlet forced-air parametric sensor electrical signals are converted into appropriate raw outlet forced-air parametric values as follows: $T_{out}(air)^{raw}=F_4[(S_T)_{out}]$, $H_{out}(air)^{raw}=F_5[(S_H)_{out}]$, and $FR_{out}(air)^{raw}=F_6[(S_{FR})_{out}]$, where $F_4$ is a linear or non-linear function of outlet forced-air temperature sensor electrical signal, $(S_T)_{out}$, $F_5$ is a linear or non-linear function of outlet forced-air humidity sensor electrical signal, $(S_H)_{out}$, and, $F_6$ is a linear or non-linear function of outlet forced-air flow rate sensor electrical signal, $(S_{FR})_{out}$, respectively. Moreover, each of the outlet air parametric functions, $F_4[(S_T)_{out}]$, $F_5[(S_H)_{out}]$, and $F_6[(S_{FR})_{out}]$, may also be a linear or non-linear function of any combination of the raw outlet forced-air parametric values, $T_{out}(air)^{raw}$, $H_{out}(air)^{raw}$, and $FR_{out}(air)^{raw}$. Raw outlet forced-air parametric values are determined at outlet conditions of the forced-air exiting solid plant matter 50 via outlet forced-air elements 26.

Step 2 results in forming (i) at least one set of raw inlet forced-air parametric values, and, (ii) at least one set of raw outlet forced-air parametric values. Accordingly, each set of raw inlet forced-air parametric values includes (1) the raw inlet forced-air temperature value, $T_{in}(air)^{raw}$, (2) the raw inlet forced-air humidity value, $H_{in}(air)^{raw}$, and (3) the raw inlet forced-air flow rate value, $FR_{in}(air)^{raw}$. Each set of raw outlet forced-air parametric values includes (1) the raw outlet forced-air temperature value, $T_{out}(air)^{raw}$, (2) the raw outlet forced-air humidity value, $H_{out}(air)^{raw}$, and (3) the raw outlet forced-air flow rate value, $FR_{out}(air)^{raw}$.

Step 2 further includes storing each of the at least one set of raw inlet forced-air parametric values, and, each of the at least one set of raw outlet forced-air parametric values, by central processing unit 44.

Preferably, there is forming and storing each set of raw inlet forced-air parametric values simultaneously to forming and storing a paired set of raw outlet forced-air parametric values, by central processing unit 44, according to operation of the electro-mechanically paired and axially aligned inlet and outlet forced-air elements 24 and 26, and corresponding sets 28 and 30 of inlet and forced-air outlet parametric sensors 32–42, respectively, as described above and illustratively shown by 52 and 54.

Step 2 preferably includes process correcting (i) each value of the at least one set of raw inlet forced-air parametric values, and, (ii) each value of the at least one set of raw outlet forced-air parametric values, for forming (i) at least one set of process corrected inlet forced-air parametric values, and, (ii) at least one set of process corrected outlet forced-air parametric values.

Process correcting of the raw forced-air parametric values, obtained and stored according to Step 1, is performed in order to account, by correcting, for the affects, typically, non-linear in nature, of secondary operating parameters of the drying or cooling forced-air treatment process during the step of sensing and measuring inlet and outlet forced-air parameters by respective inlet forced-air parametric sensors 32, 34, and 36, and outlet forced-air parametric sensors 39, 40, and 42, for generating sets of process corrected inlet and outlet forced-air parametric values while the forced-air continuously or discontinuously enters and exits device 10 and the volume of solid plant matter 50, and, while solid plant matter 50 continuously or discontinuously enters and exits device 10.

Calibration and process related empirical data obtained and stored according to operating device 10 as described above, are used in the step of process correcting the raw forced-air parametric values. Calibration and process related empirical data features, for example, determinations of moisture content and uniformity made during conditions involving well characterized and controlled primary operating parameters of forced-air temperature, T(air), humidity, H(air), and flow rate, FR(air), and, well characterized and controlled secondary operating parameters of (1) the volumetric bulk material transport rate, hereinafter referred to as $V_{Bulk}(spm)$, of solid plant matter 50 transported by solid plant matter transport mechanism 16, such as a conveyor, through drying or cooling device 10 during the on-line drying or cooling forced-air treatment, where $V_{Bulk}(spm)$ is a function of the configuration or volume of bulk solid plant matter 50 fed onto, and situated on, solid plant matter transport mechanism 16, and a function of the linear speed or velocity of solid plant matter transport mechanism 16, (2) the type, hereinafter referred to as Y(spm), of solid plant matter 10, and (3) physicochemical characteristics and properties, hereinafter referred to as D(spm), of solid plant matter 50, subjected to the drying or cooling forced-air treatment. For example, D(spm) is a function of the density, among other physicochemical characteristics and properties, of solid plant matter 50.

In particular, according to a functional relationship featuring each raw inlet forced-air parametric value and the secondary operating parameters of the drying or cooling forced-air treatment, raw inlet forced-air parametric values are process corrected for forming process corrected inlet forced-air parametric values as follows:

$$T_{in}(air)^{pc} = F_{PC1}[T_{in}(air)^{raw}, V_{Bulk}(spm), Y(spm), D(spm)],$$

$$H_{in}(air)^{pc} = F_{PC2}[H_{in}(air)^{raw}, V_{Bulk}(spm), Y(spm), D(spm)], \text{ and}$$

$$FR_{in}(air)^{pc} = F_{PC3}[FR_{in}(air)^{raw}, V_{Bulk}(spm), Y(spm), D(spm)].$$

In these relations, $F_{PC1}$, is a linear or non-linear function of the raw inlet forced-air temperature value, $T_{in}(air)^{raw}$, $V_{Bulk}(spm)$, Y(spm), and D(spm); $F_{PC2}$ is a linear or non-linear function of the raw inlet forced-air humidity value, $H_{in}(air)^{raw}$, $V_{Bulk}(spm)$, Y(spm), and D(spm); and, $F_{PC3}$ is a linear or non-linear function of the raw inlet forced-air flow rate value, $F_{in}(air)^{raw}$, $V_{Bulk}(spm)$, Y(spm), and D(spm), respectively.

Similarly, according to a functional relationship featuring each raw outlet forced-air parametric value and the secondary operating parameters of the drying or cooling forced-air treatment, raw outlet forced-air parametric values are process corrected for forming corresponding process corrected outlet forced-air parametric values as follows:

$$T_{out}(air)^{pc} = F_{PC4}[T_{out}(air)^{raw}, V_{Bulk}(spm), Y(spm), D(spm)],$$

$$H_{out}(air)^{pc} = F_{PC5}[H_{out}(air)^{raw}, V_{Bulk}(spm), Y(spm), D(spm)], \text{ and}$$

$$FR_{out}(air)^{pc} = F_{PC6}[FR_{out}(air)^{raw}, V_{Bulk}(spm), Y(spm), D(spm)].$$

In these relations, $F_{PC4}$ is a linear or non-linear function of the raw outlet forced-air temperature value, $T_{out}(air)^{raw}$, $V_{Bulk}(spm)$, Y(spm), and D(spm); $F_{PC5}$ is a linear or non-linear function of the raw outlet forced-air humidity value, $H_{out}(air)^{raw}$, $V_{Bulk}(spm)$, Y(spm), and D(spm); and, $F_{PC6}$ is a linear or non-linear function of the raw outlet forced-air flow rate value, $FR_{out}(air)^{raw}$, $V_{Bulk}(spm)$, Y(spm), and D(spm), respectively.

Step 2 results in forming (i) at least one set of process corrected inlet forced-air parametric values, and, (ii) at least one set of process corrected outlet forced-air parametric values. Accordingly, each set of process corrected inlet forced-air parametric values includes (1) the process corrected inlet forced-air temperature value, $T_{in}(air)^{pc}$, (2) the process corrected inlet forced-air humidity value, $H_{in}(air)^{pc}$, and (3) the process corrected inlet forced-air flow rate value, $FR_{in}(air)^{pc}$. Each set of process corrected outlet forced-air parametric values includes (1) the process corrected outlet forced-air temperature value, $T_{out}(air)^{pc}$, (2) the process corrected outlet forced-air humidity value, $H_{out}(air)^{pc}$, and (3) the process corrected outlet forced-air flow rate value, $FR_{out}(air)^{pc}$.

Step 2 preferably further includes storing each of the at least one set of process corrected inlet forced-air parametric values, and, each of the at least one set of process corrected outlet forced-air parametric values, by central processing unit 44.

In Step 3, there is calculating, and storing, a moisture content value of the solid plant matter, hereinafter referred to as W(spm), passing through the device, from each set of process corrected inlet forced-air parametric values and each set of process corrected outlet forced-air parametric values, obtained in Step 2.

Preferably, there is calculating and storing a moisture content value of the solid plant matter, W(spm), from each set of process corrected inlet forced-air parametric values and each paired set of process corrected outlet forced-air parametric values, by central processing unit 44, according to operation of the electro-mechanically paired and axially aligned inlet and outlet forced-air elements 24 and 26, and corresponding sets 28 and 30 of inlet and forced-air outlet parametric sensors 32–42, respectively, as described above and illustratively shown by 52 and 54.

In particular, there is calculating a plurality of moisture content values of solid plant matter 50, W(spm), passing through device 10, according to case (1) as a continuous or discontinuous function of time, t, and/or, according to case (2) as a continuous or discontinuous function of position, p, from the plurality of sets of process corrected inlet forced-air parametric values and the corresponding plurality of sets of process corrected outlet forced-air parametric values.

In case (1), for a given value of a position, Pms of solid plant matter 50 within device 10, in the range between solid plant matter inlet 12 and solid plant matter outlet 14, moisture content of solid plant matter 50 is determined as a function of time, t, by calculating the moisture content value of solid plant matter 50, W(spm), at position $p_m$ for at least two values of time, $t_n$, where m and n are each integers used for indexing specific values of position, p, and specific values of time, t, respectively. Case (1) enables generating a time profile of moisture content values, $W_t$(spm; $p_m$), for any position, $p_m$, of solid plant matter 50 subjected to the drying or cooling forced-air treatment.

Alternatively, in case (2), at a given instant of time, $t_n$, of solid plant matter 50 within device 10, in the range between solid plant matter 50 entering solid plant matter inlet 12 and exiting solid plant matter outlet 14, moisture content of solid plant matter 50 is determined as a function of position, p, by calculating the moisture content value of solid plant matter 50, W(spm), at time, $t_n$, for at least two values of position, $p_m$. Case (2) enables generating a position profile of moisture content values, $W_p$(spm; $t_n$), at any time, $t_n$, of solid plant matter 50 subjected to the drying or cooling forced-air treatment.

The method for calculating at least one moisture content value of solid plant matter 50, W(spm), passing through device 10, as a continuous or discontinuous function of time, t, according to case (1), and/or, as a continuous or discontinuous function of position, p, according to case (2), from the at least one set of process corrected inlet forced-air parametric values, process corrected inlet forced-air temperature, $T_{in}(air)^{pc}$, process corrected inlet forced-air humidity, $H_{in}(air)^{pc}$, and process corrected inlet forced-air flow rate, $FR_{in}(air)^{pc}$, and the at least one set of process corrected outlet forced-air parametric values, process corrected outlet forced-air temperature, $T_{out}(air)^{pc}$, process corrected outlet forced-air humidity, $H_{out}(air)^{pc}$, and process corrected outlet forced-air flow rate, $FR_{out}(air)^{pc}$, obtained in Step 2, is herein described according to the following sub-steps of Step 3:

In sub-step 1, of Step 3, there is obtaining, and storing, values of maximum gas phase water partial pressure, herein, equivalently referred to as maximum water partial pressure, $P^{max}$(water), corresponding to the saturation pressure of gas phase water, in the forced-air, capable of entering with process corrected inlet forced-air temperature value, $T_{in}(air)^{pc}$, and capable of exiting with process corrected outlet forced-air temperature value, $T_{out}(air)^{pc}$, solid plant matter 50, hereinafter referred to as $P^{max}_{in}$(water), and, $P^{max}_{out}$(water), respectively, preferably, by central processing unit 44.

$P^{max}_{in}$(water) and $P^{max}_{out}$(water) may be obtained by calculation or by using a look-up-table. By calculation, there is evaluating any one of a variety of known standard functional relationships, hereinafter referred to as $F_7[T(air)]$, between the saturation pressure of water in air, $P^{max}$(water), and air temperature, T(air), at the process corrected inlet forced-air temperature value, $T_{in}(air)^{pc}$, and, at the process corrected outlet forced-air temperature value, $T_{out}(air)^{pc}$, whereby $P^{max}_{in}$(water)=$F_7[T(air)$; for $T(air)=T_{in}(air)^{pc}]$, and, $P^{max}_{out}$(water)=$F_7[T(air)$; for $T(air)=T_{out}(air)^{pc}]$, respectively. Alternatively, $P^{max}_{in}$(water) and $P^{max}_{out}$(water), may be obtained by central processing unit 44 identifying and selecting the value of $P^{max}$(water) at the process corrected inlet forced-air temperature value, $T_{in}(air)^{pc}$, and, $P^{max}$(water) at the process corrected outlet forced-air temperature value, $T_{out}(air)^{pc}$, from a database stored as part of central processing unit 44, featuring calculated or empirical values of saturation pressure of water, $P^{max}$(water), versus air temperature, T(air), obtained from an appropriate look-up-table. The values of $P^{max}_{in}$(water) and $P^{max}_{out}$(water) are then stored by central processing unit 44.

In sub-step 2, of Step 3, there is calculating, and storing, values of maximum gas phase water concentration, herein, equivalently referred to as maximum water concentration, $C^{max}$(water), corresponding to the saturation concentration of gas phase water, in the forced-air, capable of entering with process corrected inlet forced-air temperature value, $T_{in}(air)^{pc}$, and capable of exiting with process corrected outlet forced-air temperature value, $T_{out}(air)^{pc}$, solid plant matter 50, hereinafter referred to as $C^{max}_{in}$(water), and, $C^{max}_{out}$(water), respectively, preferably, by central processing unit 44.

$C^{max}_{in}$(water) and $C^{max}_{out}$(water) are obtained by calculation, by evaluating any one of a variety of known standard functional relationships, hereinafter referred to as $F_8[P(water), T(air)]$, relating the water concentration in air, C(water), to the water partial pressure in air, P(water), and the air temperature, T(air), according to C(water)=$F_8[P(water), T(air)]$, where C(water) is expressed in dimensions of mass of water per unit volume of air. Accordingly, $C^{max}_{in}$(water) $F_8[P(water), T(air)$; for $P(water)=P^{max}_{in}$(water), and $T(air)=T_{in}(air)^{pc}]$, and, $C^{max}_{out}$(water)=$F_8[P(water), T(air)$; for $P(water)=P^{max}_{out}$(water), and $T(air)=T_{out}(air)^{pc}]$, respectively.

For the assumption that the water in the forced-air behaves as an ideal gas, entering and exiting the volume of solid plant matter 50, during the drying or cooling forced-air treatment, the standard 'ideal gas law', PV=nRT, where P is the partial pressure of n moles of a gas within volume V, at temperature T, and R is the universal gas constant, can be used for obtaining the functional relationship, $F_8[P(water), T(air)]$, relating the water concentration in the forced-air, C(water), to the water partial pressure in the forced-air, P(water), and the forced-air temperature, T(air). Accordingly, n/V=m/(MV)=P/(RT), where m is the mass and M is the mass molecular weight, of the gas at temperature, T. For the gas concentration expressed in dimensions of mass per unit volume, C=m/V=(MP)/(RT), thus, $F_8[P(water), T(air)]=[M(water)P(water)]/[RT(air)]$, and, C(water)=$[(M(water)P(water)]/[RT(air)]$. Therefore, $C^{max}_{in}$(water) and $C^{max}_{out}$(water) are obtained by evaluating the following formulas:

$C^{max}_{in}(\text{water}) = [M(\text{water}) P^{max}_{in}(\text{water})]/[RT_{in}(\text{air})^{pc}]$, and similarly, $C^{max}_{out}(\text{water}) = [M(\text{water}) P^{max}_{out}(\text{water})]/[RT_{out}(\text{air})^{pc}]$, where $P^{max}_{in}(\text{water})$ and $P^{max}_{out}(\text{water})$ are obtained from sub-step 1. The values of $C^{max}_{in}(\text{water})$ and $C^{max}_{out}(\text{water})$ are then stored by central processing unit 44.

In sub-step 3, of Step 3, there is calculating, and storing, values of actual water concentration, $C^{actual}(\text{water})$, in the forced-air, entering with process corrected inlet forced-air temperature value, $T_{in}(\text{air})^{pc}$, and exiting with process corrected outlet forced-air temperature value, $T_{out}(\text{air})^{pc}$, solid plant matter 50, hereinafter referred to as $C^{actual}_{in}(\text{water})$, and, $C^{actual}_{out}(\text{water})$, respectively, preferably, by central processing unit 44.

Applying the same analysis used in sub-step 2, $C^{actual}_{in}(\text{water})$, and, $C^{actual}_{out}(\text{water})$, are obtained by evaluating the formulas, $C^{actual}_{in}(\text{water}) = [M(\text{water}) P^{actual}_{in}(\text{water})]/[RT_{in}(\text{air})^{pc}]$, and similarly, $C^{actual}_{out}(\text{water}) = [M(\text{water}) P^{actual}_{out}(\text{water})]/[RT_{out}(\text{air})^{pc}]$, where $P^{actual}_{in}(\text{water})$ and $P^{actual}_{out}(\text{water})$ correspond to actual water partial pressure in the forced-air, entering and exiting, respectively, the volume of solid plant matter 50, during the drying or cooling forced-air treatment.

For evaluating these formulas, the values of actual water partial pressure in the forced-air, $P^{actual}_{in}(\text{water})$ and $P^{actual}_{out}(\text{water})$, entering and exiting, respectively, the volume of solid plant matter 50, are related to the values of maximum water partial pressure in the forced-air, $P^{max}_{in}(\text{water})$ and $P^{max}_{out}(\text{water})$, capable of entering and exiting, respectively, the volume of solid plant matter 50, obtained from sub-step 1, by using the empirically determined process corrected forced-air parametric values of humidity entering and exiting the volume of solid plant matter 50 during the drying or cooling forced-air treatment, process corrected inlet forced-air humidity value, $H_{in}(\text{air})^{pc}$, and process corrected outlet forced-air humidity value, $H_{out}(\text{air})^{pc}$, respectively, obtained through Step 6, and stored by central processor unit 44.

Since water partial pressure in the forced-air, P(water), is directly proportional to humidity of the forced-air, H(air), $[P^{actual}_{in}(\text{water})/P^{max}_{in}(\text{water})] = [H^{actual}_{in}(\text{air})/H^{max}_{in}(\text{air})]$, and, $[P^{actual}_{out}(\text{water})/P^{max}_{out}(\text{water})] = [H^{actual}_{out}(\text{air})/H^{max}_{out}(\text{air})]$, where $H^{actual}_{in}(\text{air})$ and $H^{max}_{in}(\text{air})$ correspond to actual and maximum inlet forced-air humidity values, respectively, and, $H^{actual}_{out}(\text{air})$ and $H^{max}_{out}(\text{air})$ correspond to actual and maximum outlet forced-air humidity values, respectively. Accordingly, $P^{actual}_{in}(\text{water}) = P^{max}_{in}(\text{water}) [H^{actual}_{in}(\text{air})/H^{max}_{in}(\text{air})]$, and, $P^{actual}_{out}(\text{water}) = P^{max}_{out}(\text{water}) [H^{actual}_{out}(\text{air})/H^{max}_{out}(\text{air})]$.

In these formulas, $H^{actual}_{in}(\text{air})$ and $H^{actual}_{out}(\text{air})$ are equivalent to the empirically determined process corrected forced-air parametric values of humidity, $H_{in}(\text{air})^{pc}$, and $H_{out}(\text{air})^{pc}$, respectively, obtained through Step 2, during actual operation of the method and device or the present invention, and, $H^{max}_{in}(\text{air})$ and $H^{max}_{out}(\text{air})$ are empirically determined by operating the method and device of the present invention, through Step 2, at established maximum humidity forced-air values, but at the same process corrected forced-air temperature and flow rate values, $T_{in}(\text{air})^{pc}$, $T_{out}(\text{air})^{pc}$, $FR_{in}(\text{air})^{pc}$, and $FR_{out}(\text{air})^{pc}$, used for measuring the actual $H_{in}(\text{air})^{pc}$ and $H_{out}(\text{air})^{pc}$, for obtaining the maximum values of inlet and outlet forced-air humidity. These formulas for $P^{max}_{in}(\text{water})$ and $P^{max}_{out}(\text{water})$ are now used in the previously described formulas for $C^{actual}_{in}(\text{water})$, and $C^{actual}_{out}(\text{water})$, respectively, as follows:

$C^{actual}_{in}(\text{water}) = [M(\text{water}) P^{max}_{in}(\text{water}) H_{in}(\text{air})^{pc}]/[RT_{in}(\text{air})^{pc} H^{max}_{in}(\text{air})]$, and similarly, $C^{actual}_{out}(\text{water}) = [M(\text{water}) P^{max}_{out}(\text{water}) H_{out}(\text{air})^{pc}]/[RT_{out}(\text{air})^{pc} H^{max}_{out}(\text{air})]$, where a value for each term of these formulas is previously determined and stored by central processing unit 44. The values of $C^{actual}_{in}(\text{water})$ and $C^{actual}_{out}(\text{water})$ are then stored by central processing unit 44.

In sub-step 4, of Step 3, there is determining the implementing or operating status, as 'normal' or 'abnormal', of the method and device for determining the moisture content and uniformity of solid plant matter 50 during the on-line drying or cooling forced-air treatment, preferably, by central processing unit 44.

Determining the implementing or operating status, herein, referred to as the implementing status, represents a built-in automatic quality control checking procedure during implementation or operation of the method and device 10 of the present invention. Normal, or, abnormal, implementing status corresponds to animal, or, abnormal, implementation or operation of the method and device 10, in general, and any number or combination of method steps and sub-steps, and device units, mechanisms, elements, and components, in particular. This includes, for example, the presence of all normal, or, one or more abnormal, values of data and/or information input into central processing unit 44, and for example, normal, or, abnormal, operation of device 10. For the condition of a normal implementing status, implementation or operation of the method and device 10 continue for determining the moisture content and uniformity of solid plant matter 50 during the on-line drying or cooling forced-air treatment. For the condition of an abnormal implementing status, there is indicating, by central processing unit 44, that implementation or operation of the method and device 10 is abnormal, leading to checking the method and device 10 by an operator, an inspecting device, or both (not illustrated).

For performing sub-step 4, of Step 3, there is calculating and assigning, values of the quality, $Q[C^{actual}(\text{water})]$, of the values of the actual water concentration in the forced-air, entering and exiting solid plant matter 50, $C^{actual}_{in}(\text{water})$ and $C^{actual}_{out}(\text{water})$, respectively, at the process corrected inlet and outlet forced-air temperature values, humidity values, and flow rate values, $T_{in}(\text{air})^{pc}$, $H_{in}(\text{air})^{pc}$, $FR_{in}(\text{air})^{pc}$, and, $T_{out}(\text{air})^{pc}$, $H_{out}(\text{air})^{pc}$, and $FR_{in}(\text{air})^{pc}$, respectively, hereinafter referred to as $Q_{in}[C^{actual}_{in}(\text{water})]$, and, $Q_{out}[C^{actual}_{out}(\text{water})]$, respectively, preferably, by central processing unit 44.

The quality, $Q[C^{actual}(\text{water})]$, is herein defined as the ratio of the value of the actual water concentration in the forced-air, $C^{actual}(\text{water})$, to the value of the maximum water concentration in the forced-air, $C^{max}(\text{water})$, at the process corrected forced-air temperature values, such that, $Q[C^{actual}(\text{water})] = [C^{actual}(\text{water})/C^{max}(\text{water})]$. Accordingly, the following formulas are used for calculating and assigning values of the quality of the actual water concentration in the forced-air entering and exiting solid plant matter 50 during the drying or cooling forced-air treatment:

$Q[C^{actual}_{in}(\text{water})] = [C^{actual}_{in}(\text{water})/C^{max}_{in}(\text{water})]$, and, $Q[C^{actual}_{out}(\text{water})] = [C^{actual}_{out}(\text{water})/C^{actual}_{out}(\text{water})]$.

During normal implementation of the method and device 10 of the present invention, for a given set of process corrected forced-air parametric values, the value of the actual water concentration in the forced-air, $C^{actual}(\text{water})$, is less than or equal to, the value of the maximum water concentration in the forced-air, $C^{max}(\text{water})$, such that the value of the quality of the actual water concentration in the forced-air, $Q[C^{actual}_{in}(water)]$, is less than or equal to one, and this value is assigned as a 'normal implementing status' by central processing unit 44. At forced-air parametric conditions where the value of the actual water concentration is equal to the value of the maximum water concentration, corresponding to water saturation in the forced-air, $C^{actual}(water)$ equals $C^{max}(water)$, such that $Q[C^{actual}(water)]$ is equal to one, this value is also assigned as a 'normal implementing status' by central processing unit 44. If the value of the actual water concentration is greater than the value of the maximum water concentration, in the forced-air, whereby, $C^{actual}(water)$ is greater than $C^{max}(water)$, such that $Q[C^{actual}(water)]$ is greater than one, this value is assigned as an 'abnormal implementing status' by central processing unit 44.

Therefore, determining the implementing status of the method and device 10 is according to fulfillment of one of the following four conditions:

1. For both $Q[C^{actual}_{in}(water)]$, and, $Q[C^{actual}_{out}(water)]$, less than one, the implementing status is assigned as normal, and implementation of the method and device 10 continues with sub-step 5, of Step 3.
2. For both $Q[C^{actual}_{in}(water)]$, and, $Q[C^{actual}_{out}(water)]$, equal to one, the implementing status is assigned as normal, and implementation of the method and device 10 continues with sub-step 5, of Step 3.
3. For either $Q[C^{actual}_{in}(water)]$, or, $Q[C^{actual}_{out}(water)]$, greater than one, the implementing status is assigned as abnormal, and implementation of the method and device 10 continues with checking the method and device 10 by an operator, an inspecting device, or both.
4. For both $Q[C^{actual}_{in}(water)]$, and, $Q[C^{actual}_{out}(water)]$, greater than one, the implementing status is assigned as abnormal, and implementation of the method and device 10 continues with checking the method and device 10 by an operator, an inspecting device, or both.

In sub-step 5, of Step 3, there is calculating, and storing, the at least one moisture content value of solid plant matter 50, W(spm), passing through device 10, during the on-line drying or cooling forced-air treatment, from values of the actual water concentration in the forced-air, entering and exiting solid plant matter 50, $C^{actual}_{in}(water)$ and $C^{actual}_{out}(water)$, respectively, at the process corrected inlet and outlet forced-air temperature values, humidity values, and flow rate values, $T_{in}(air)^{pc}$, $H_{in}(air)^{pc}$, $FR_{in}(air)^{pc}$, and, $T_{out}(air)^{pc}$, $H_{out}(air)^{pc}$, and $FR_{out}(air)^{pc}$, respectively, preferably, by central processing unit 44.

Moisture content of solid plant matter 50, W(spm), is calculated by evaluating a linear or nonlinear function of the actual water concentration in the forced-air, entering and exiting solid plant matter 50, $C^{actual}_{in}(water)$ and $C^{actual}_{out}(water)$, respectively, hereinafter referred to as $F_9[C^{actual}_{in}(water), C^{actual}_{out}(water)]$, at the process corrected inlet and outlet forced-air temperature values, humidity values, and flow rate values, such that $W(spm)=F_9[C^{actual}_{in}(water), C^{actual}_{out}(water)]$, where W(spm) is evaluated as a percent.

W(spm), as a percent, is proportional to the ratio of the mass of water present in solid plant matter 50 to the mass of solid plant matter 50 in a state or form of dryness.

W(spm)=100×(mass of the water in the solid plant matter)/(mass of the dry solid plant matter).

The following form of $F_9[C^{actual}_{in}(water), C^{actual}_{out}(water)]$ is used for calculating values of moisture content of solid plant matter 50:

$$W(spm)=k_1[C^{actual}_{in}(water)+[(C^{actual}_{out}(water)-C^{actual}_{in}(water))/(k_2 k_3)^f]].$$

In this formula for W(spm), $k_1$, $k_2$, and $k_3$, are empirically determined constants, and f is a linear or nonlinear function of the process corrected outlet forced-air flow rate value, $FR_{out}(air)^{pc}$, such that $f=F_{10}[FR_{out}(air)^{pc}]$. An exemplary form of $F_{10}[FR_{out}(air)^{pc}]$ is $FR_{out}(air)^{pc}$ raised to the power of h, or $[FR_{out}(air)^{pc}]^h$, where h is an empirically determined constant.

Values of $C^{actual}_{in}(water)$ and $C^{actual}_{out}(water)$, at the process corrected inlet and outlet forced-air parametric conditions, were determined and stored by central processing unit 44, according to sub-steps 1–3, of Step 3, and values of $FR_{out}(air)^{pc}$ were determined and stored by central processing unit 44, through Step 2. Thus, all data needed for evaluating the formula of W(spm) are known.

In Step 4, there is calculating, and storing, a uniformity value of solid plant matter 50, hereinafter referred to as U(spm), passing through device 10, from at least two moisture content values, W(spm), calculated in Step 3, preferably, by central processing unit 44. Preferably, there is calculating a uniformity value of the solid plant matter, U(spm), from at least two moisture content values which are calculated from the at least one set of process corrected inlet air parametric values and the at least one paired set of process corrected outlet air parametric values, by central processing unit 44, according to operation of the electro-mechanically paired and axially aligned inlet and outlet forced-air elements 24 and 26, and corresponding sets 28 and 30 of inlet and forced-air outlet parametric sensors 32–42, respectively, as described above and illustratively shown by 52 and 54.

In particular, there is calculating a plurality of uniformity values of solid plant matter 50, U(spm), passing through device 10, according to case (1) as a continuous or discontinuous function of time, t, and/or, according to case (2) as a continuous or discontinuous function of position, p, from the plurality of moisture content values calculated and stored according to Step 3.

In case (1), for a given value of a position, Pm, of solid plant matter 50 within device 10, in the range between solid plant matter inlet 12 and solid plant matter outlet 14, uniformity of solid plant matter 50 is determined as a function of time, t, from at least two moisture content values, $W_t(spm; p_m)$, obtained from the previously determined time profile of moisture content values. Case (1) enables generating a time profile of uniformity values, $U_t(spm; p_m)$, for any position $p_m$, of solid plant matter 50 subjected to the drying or cooling forced-air treatment.

Alternatively, in case (2), at a given instant of time, t, of solid plant matter 50 within device 10, in the range between solid plant matter 50 entering solid plant matter inlet 12 and exiting solid plant matter outlet 14, uniformity of solid plant matter 50 is determined as a function of position, p, from at least two moisture content values, $W_p(spm; t_n)$, obtained from the previously determined position profile of moisture content values. Case (2) enables generating a position profile of uniformity values, $U_p(spm; t_n)$, at any time, $t_n$, of solid plant matter 50 subjected to the drying or cooling forced-air treatment.

Standard techniques of statistical analysis can be used for calculating uniformity values, U(spm), of solid plant matter 50 from moisture content values, W(spm), of solid plant matter 50. For example, in case (1), the time profile of uniformity values, $U_t(spm; p_m)$ for any position, $p_m$, of solid plant matter 50 subjected to the drying or cooling forced-air treatment, can be generated by evaluating a plurality of ratios of a moisture content value, $W_t(\text{spm}; p_m)$, to the average of at least two moisture content values, $[W_t(\text{spm}; p_m)]_{average}$, for the position $p_m$, such that:

$$U_t(\text{spm}; p_m) = [W_t(\text{spm}; p_m)]/[W_t(\text{spm}; p_m)]_{average},$$

Alternatively, in case (2), the position profile of uniformity values, $U_p(\text{spm}; t_n)$, at any time, $t_n$, of solid plant matter 50 subjected to the drying or cooling forced-air treatment, can be generated by evaluating a plurality of ratios of a moisture content value, $W_p(\text{spm}; t_n)$, to the average of at least two moisture content values, $[W_p(\text{spm}; t_n)]_{average}$, at time, $t_n$, such that:

$$U_p(\text{spm}; t_n) = [W_p(\text{spm}; t_n)]/[W_p(\text{spm}; t_n)]_{average},$$

The method and device of the present invention enable determining values of moisture content and uniformity corresponding to the entire volume of moving solid plant matter, based on accurately and reproducibly measuring a multiple of operating parameters during the drying or cooling forced-air treatment. These values are appropriately used for achieving high levels of process optimization and control of the drying or cooling forced-air treatment, thereby contributing to optimization and control of an overall manufacturing sequence for producing consumer end products containing solid plant matter raw materials.

While the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for non-invasively determining moisture content and uniformity of solid plant matter during on-line drying or cooling forced-air treatment, comprising the steps of:

(a) sensing and measuring forced-air operating parameters while forced-air enters and exits the solid plant matter, said forced-air operating parameters include temperature, humidity, and flow rate;

(b) processing said forced-air operating parameters for forming forced-air parametric values, said forced-air parametric values include forced-air temperature values, forced-air humidity values, and forced-air flow rate values;

(c) calculating a moisture content value of the solid plant matter from said forced-air parametric values; and (d) calculating a uniformity value of the solid plant matter from at least two said moisture content values of the solid plant matter.

2. The method of claim 1, whereby said forced-air is at conditions corresponding to those selected from the group consisting of laminar flow and turbulent flow, said conditions selected by varying said forced-air operating parameters.

3. The method of claim 1, whereby said temperature, humidity, and flow ate forced-air operating parameters are simultaneously sensed and measured.

4. The method of claim 1, whereby said temperature, humidity, and flow rate forced-air operating parameters are simultaneously processed.

5. The method of claim 1, whereby said sensing and measuring said forced-air operating parameters are effected by a device including forced-air parametric sensors, said forced-air parametric sensors include a forced-air temperature sensor, a forced-air humidity sensor, and a forced-air flow rate sensor.

6. The method of claim 1, whereby said sensing and measuring said forced-air operating parameters further includes generating forced-air parametric sensor electrical signals, said forced-air parametric sensor electrical signals include a forced-air temperature sensor electrical signal, a forced-air humidity sensor electrical signal, and a forced-air flow rate sensor electrical signal.

7. The method of claim 6, whereby each said forced-air parametric sensor electrical signal is a function of at least one said forced-air operating parameter.

8. The method of claim 6, whereby said forced-air parametric sensor electrical signals are converted into raw forced-air parametric values, said raw forced-air parametric values include a raw forced-air temperature value, a raw forced-air humidity value, and a raw forced-air flow rate value.

9. The method of claim 8, whereby said raw forced-air parametric values are process corrected for generating process corrected forced-air parametric values for generating process corrected forced-air parametric values, said process corrected forced-air parametric values include a process corrected forced-air temperature value, a process corrected forced-air humidity value, and a process corrected forced-air flow rate value.

10. The method of claim 9, whereby said process correcting of said raw forced-air parametric values accounts for affects of at least one secondary operating parameter on the step of said sensing and measuring said forced-air operating parameters of temperature, humidity, and flow rate.

11. The method of claim 10, whereby said at least one secondary operating parameter is selected from the group consisting of volumetric bulk transport rate of the solid plant matter, type of the solid plant matter, and, physical characteristics and properties of the solid plant matter.

12. The method of claim 11, whereby said volumetric bulk transport rate of the solid plant matter corresponds to volumetric rate at which the solid plant matter in bulk form is transported by a transport mechanism through a drying or cooling device during the on-line drying or cooling forced-air treatment, said volumetric transport rate is a function of a parameter selected from the group consisting of configuration and volume of said bulk form of the solid plant matter fed onto and situated on said transport mechanism and is a function of linear speed of said transport mechanism moving the solid plant matter through said drying or cooling device.

13. The method of claim 11, whereby said type of the solid plant matter is selected from the group consisting of leaves, beans, seeds, grains, flowers, stems, stalks, and roots, said type of the solid plant matter is in a form selected from the group consisting of raw, processed, loose and web.

14. The method of claim 11, whereby said physical characteristics and properties of the solid plant matter include density of the solid plant matter.

15. The method of claim 1, whereby the step of processing each said forced-air operating parameter includes accounting for affects of a remainder of said operating parameters on said sensing and measuring each said operating parameter.

16. The method of claim 1, whereby the step of forming said forced-air parametric values includes forming raw forced-air parametric values followed by forming process corrected forced-air parametric values, by process correcting said raw forced-air parametric values, where raw forced-air parametric values include a raw forced-air temperature value, a raw forced-air humidity value, and a raw forced-air flow rate value, and where said process corrected forced-air parametric values include a process corrected forced-air temperature value, a process corrected forced-air humidity value, and a process corrected forced-air flow rate value.

17. The method of claim 16, whereby said process correcting of said raw forced-air parametric values accounts for affects of at least one secondary operating parameter on the step of said sensing and measuring said forced-air operating parameters of temperature, humidity, and flow rate.

18. The method of claim 17, whereby said at least one secondary operating parameter is selected from the group consisting of volumetric bulk transport rate of the solid plant matter, type of the solid plant matter, and, physical characteristics and properties of the solid plant matter.

19. The method of claim 18, whereby said volumetric bulk transport rate of the solid plant matter corresponds to volumetric rate at which the solid plant matter in bulk form is transported by a transport mechanism through a drying or cooling device during the on-line drying or cooling forced-air treatment, said volumetric transport rate is a function of a parameter selected from the group consisting of configuration and volume of said bulk form of the solid plant matter fed onto and situated on said transport mechanism and is a function of linear speed of said transport mechanism moving the solid plant matter through said drying or cooling device.

20. The method of claim 18, whereby said type of the solid plant matter is selected from the group consisting of leaves, beans, seeds, grains, flowers, stems, stalks, and roots, said type of the solid plant matter is in a form selected from the group consisting of raw, processed, loose and web.

21. The method of claim 18, whereby said physical characteristics and properties of the solid plant matter include density of the solid plant matter.

22. The method of claim 1, whereby said moisture content value of the solid plant matter is calculated as a function of a parameter selected from the group consisting of time during the on-line forced-air treatment and position of the solid plant matter during the on-line forced-air treatment.

23. The method of claim 1, whereby said calculating said moisture content value of the solid plant matter further includes generating a profile selected from the group consisting of a position profile of a plurality of said moisture content values at an instant of time during the on-line forced-air treatment and a time profile of said moisture content values for a position of the solid plant matter during the on-line forced-air treatment.

24. The method of claim 1, whereby the step of said calculating said moisture content of the solid plant matter from forced-air parametric values comprises the steps of:
  (i) obtaining values of maximum water partial pressure corresponding to saturation pressure of water in said forced-air capable of entering the solid plant matter with an inlet forced-air temperature value and exiting the solid plant matter with an outlet forced-air temperature value;
  (ii) calculating values of maximum water concentration corresponding to saturation concentration of water in said forced-air capable of entering the solid plant matter with said inlet forced-air temperature value and exiting the solid plant matter with said outlet forced-air temperature value, from said values of maximum water pressure capable of entering and exiting the solid plant matter;
  (iii) calculating values of actual water concentration in said forced-air entering the solid plant matter with said inlet forced-air temperature value and an inlet forced-air humidity value and exiting the solid plant matter with said outlet forced-air temperature value and an outlet forced-air humidity value, from said values of maximum water pressure capable of entering and exiting the solid plant matter;
  (iv) determining an implementing status of the method for determining the moisture content and uniformity of the solid plant matter during the on-line drying or cooling forced-air treatment; and
  (v) calculating said moisture content value of the solid plant matter from said values of said actual water concentration in said forced-air entering and exiting the solid plant matter and from said forced-air flow rate values.

25. The method of claim 24, whereby the step of obtaining said values of said maximum water partial pressure includes evaluating a function relating said saturation pressure of water in air to temperature of said air at said inlet forced-air temperature value and at said outlet forced-air temperature value.

26. The method of claim 24, whereby the step of obtaining said values of said maximum water partial pressure includes identifying and selecting said values of said maximum water partial pressure at said inlet forced-air temperature value and at said outlet forced-air temperature value from a look-up-table featuring values of said saturation pressure of water in air versus temperature of said air.

27. The method of claim 24, whereby the step of calculating said values of said maximum water concentration includes evaluating a function relating water concentration in air to water partial pressure in said air and temperature of said air at said inlet forced-air temperature value and at said outlet forced-air temperature value.

28. The method of claim 27, whereby said function is a form of the ideal gas law relating said water concentration in said air to molecular weight of said water in said air, said water partial pressure in said air, said temperature of said air, and the universal gas constant, said function is evaluated at said values of said maximum water pressure capable of entering and exiting the solid plant matter.

29. The method of claim 24, whereby the step of calculating said values of said actual water concentration includes evaluating a function relating water concentration in air to water partial pressure in said air, humidity of said air and temperature of said air at said inlet forced-air temperature value and at said outlet forced-air temperature value.

30. The method of claim 29, whereby said function is a form of the ideal gas law relating said water concentration in said air to molecular weight of said water in said air, said water partial pressure in said air, humidity of said air, said temperature of said air, and the universal gas constant, said function is evaluated at said values of said maximum water pressure capable of entering and exiting the solid plant matter, and at said inlet and said outlet forced-air humidity values.

31. The method of claim 24, whereby the step of said determining said implementing status of the method includes calculating and assigning values of quality of said values of said actual water concentration in said forced-air entering and exiting the solid plant matter, at said inlet and said outlet forced-air parametric values, said quality defined as the ratio of said value of said actual water concentration in said forced-air to said value of said maximum water concentration in said forced-air at said forced-air temperature values.

32. The method of claim 31, whereby for said value of said actual water concentration in said forced-air selected from the group consisting of less than and equal to said value of said maximum water concentration in said forced-air, such that said value of said quality of said actual water concentration in said forced-air is selected from the group consisting of less than one and equal to one, then said value of said quality is assigned as a normal implementing status, and there is continuing implementing the method with said step (v).

33. The method of claim 31, whereby for said value of said actual water concentration in said forced-air greater than said value of said maximum water concentration in said forced-air, such that said value of said quality of said actual water concentration in said forced-air is greater than one, then said value of said quality is assigned as an abnormal implementing status, and there is continuing implementing the method with checking the method by at least one selected from the group consisting of an operator of the on-line drying or cooling forced-air treatment and an inspecting device.

34. The method of claim 24, whereby the step of said calculating said moisture content value of the solid plant matter includes evaluating a function of said actual water concentration in said forced-air entering and exiting the solid plant matter and of said forced-air flow rate values.

35. The method of claim 34, whereby said function is of form:

$$W(spm)=k_1[C^{actual}_{in}(water)+[(C^{actual}_{out}(water)-C^{actual}_{in}(water))/(k_2k_3)^f]],$$

wherein said W(spm) is said moisture content value of the solid plant matter, said $C^{actual}_{in}(water)$ is said actual water concentration in said forced-air entering the solid plant matter, said $C^{actual}_{out}(water)$ is said actual water concentration in said forced-air exiting the solid plant matter, said $k_1$, said $k_2$, and said $k_3$, are empirically determined constants, and said f is a function of said forced-air flow rate values, said moisture content value is evaluated as a percent and is proportional to a ratio of mass of said water present in the solid plant matter to mass of the solid plant matter without water.

36. The method of claim 35, whereby said f is a function of form: $FR_{out}(air)$ raised to power of h, equivalent to $[FR_{out}(air)]^h$, where said $FR_{out}(air)$ is a said forced-air flow rate value of said forced-air exiting the solid plant matter, and said h is an empirically determined constant.

37. The method of claim 1, whereby said uniformity value of the solid plant matter calculated from said at least two said moisture content values is calculated as a function of a parameter selected from the group consisting of time during the on-line forced-air treatment and position of the solid plant matter during the on-line forced-air treatment.

38. The method of claim 1, whereby said calculating said uniformity value of the solid plant matter from said at least two said moisture content values of the solid plant matter further includes generating a profile selected from the group consisting of a position profile of a plurality of said uniformity values at an instant of time during the on-line forced-air treatment and a time profile of said uniformity values for a position of the solid plant matter during the on-line forced-air treatment.

39. The method of claim 1, whereby the step of said calculating said uniformity value of the solid plant matter from said at least two said moisture content values of the solid plant matter is performed by using techniques of statistical analysis.

40. The method of claim 1, whereby said uniformity value of the solid plant matter is evaluated from a plurality of ratios of said moisture content value of the solid plant matter to an average of said at least two said moisture content values of the solid plant matter, using a formula of form:

$U(spm)=[W(spm)]/[W(spm)]_{average}$, where said $U(spm)$ is said uniformity value of the solid plant matter, said $[W(spm)]$ is said moisture content value of the solid plant matter, and said $[W(spm)]_{average}$, is said average of said at least two said moisture content values of the solid plant matter.

41. The method of claim 1, whereby the steps of said sensing and measuring said forced-air operating parameters, said processing said forced-air operating parameters, said calculating said moisture content value of the solid plant matter, and said calculating said uniformity value from said at least two said moisture content values of the solid plant matter, are performed by a central processing unit.

42. The method of claim 1, whereby a plurality of values selected from the group consisting of said moisture content values and said uniformity values is used for achieving high levels of process optimization and control of the drying or cooling forced-air treatment, thereby contributing to optimization and control of an overall manufacturing sequence for producing consumer end products including the solid plant matter as a raw material.

43. A method for non-invasively determining moisture content and uniformity of solid plant matter during on-line drying or cooling forced-air treatment, comprising the steps of:

(a) sensing and measuring at least one set of inlet forced-air operating parameters and at least one set of outlet forced-air operating parameters, while forced-air enters and exits the solid plant matter, each said set of said forced-air operating parameters includes temperature, humidity, and flow rate;

(b) processing each said set of inlet forced-air operating parameters and each set of outlet forced-air operating parameters, for forming at least one set of inlet forced-air parametric values and at least one set of outlet forced-air parametric values;

(c) calculating a moisture content value of the solid plant matter from each said set of inlet forced-air parametric values and each said set of outlet forced-air parametric values; and (d) calculating a uniformity value of the solid plant matter from at least two said moisture content values of the solid plant matter.

44. The method of claim 43, whereby said forced-air is at conditions corresponding to those selected from the group consisting of laminar flow and turbulent flow, said conditions selected by varying said forced-air operating parameters.

45. The method of claim 43, whereby said temperature, humidity, and flow rate forced-air operating parameters are simultaneously sensed and measured.

46. The method of claim 43, whereby said temperature, humidity, and flow rate forced-air operating parameters are simultaneously processed.

47. The method of claim 43, whereby the step of processing each said set of forced-air operating parameters includes accounting for affects of a remainder of said operating parameters on said sensing and measuring each said operating parameter.

48. The method of claim 43, whereby the step of forming each said set of forced-air parametric values includes forming a set of raw forced-air parametric values followed by forming a set of process corrected forced-air parametric values, by process correcting each said set of raw forced-air parametric values, where each said set of raw forced-air parametric values includes a raw forced-air temperature value, a raw forced-air humidity value, and a raw forced-air flow rate value, and where each said set of process corrected forced-air parametric values includes a process corrected forced-air temperature value, a process corrected forced-air humidity value, and a process corrected forced-air flow rate value.

49. The method of claim 48, whereby said process correcting of said raw forced-air parametric values accounts for affects of at least one secondary operating parameter on the step of said sensing and measuring said forced-air operating parameters of temperature, humidity, and flow rate.

50. The method of claim 49, whereby said at least one secondary operating parameter is selected from the group consisting of volumetric bulk transport rate of the solid plant matter, type of the solid plant matter, and, physical characteristics and properties of the solid plant matter.

51. The method of claim 50, whereby said volumetric bulk transport rate of the solid plant matter corresponds to volumetric rate at which the solid plant matter in bulk form is transported by a transport mechanism through a drying or cooling device during the on-line drying or cooling forced-air treatment, said volumetric transport rate is a function of a parameter selected from the group consisting of configuration and volume of said bulk form of the solid plant matter fed onto and situated on said transport mechanism and is a function of linear speed of said transport mechanism moving the solid plant matter through said drying or cooling device.

52. The method of claim 50, whereby said type of the solid plant matter is selected from the group consisting of leaves, beans, seeds, grains, flowers, stems, stalks, and roots, said type of the solid plant matter is in a form selected from the group consisting of raw, processed, loose and web.

53. The method of claim 50, whereby said physical characteristics and properties of the solid plant matter include density of the solid plant matter.

54. The method of claim 43, whereby said moisture content value of the solid plant matter is calculated as a function of a parameter selected from the group consisting of time during the on-line forced-air treatment and position of the solid plant matter during the on-line forced-air treatment.

55. The method of claim 43, whereby said calculating said moisture content value of the solid plant matter further includes generating a profile selected from the group consisting of a position profile of a plurality of said moisture content values at an instant of time during the on-line forced-air treatment and a time profile of said moisture content values for a position of the solid plant matter during the on-line forced-air treatment.

56. The method of claim 43, whereby the step of said calculating said moisture content of the solid plant matter from each said set of inlet forced-air parametric values and each said set of outlet forced-air parametric values comprises the steps of:
(i) obtaining values of maximum water partial pressure corresponding to saturation pressure of water in said forced-air capable of entering the solid plant matter with said inlet forced-air temperature value and exiting the solid plant matter with said outlet forced-air temperature value;
(ii) calculating values of maximum water concentration corresponding to saturation concentration of water in said forced-air capable of entering the solid plant matter with said inlet forced-air temperature value and exiting the solid plant matter with said outlet forced-air temperature value, from said values of maximum water pressure capable of entering and exiting the solid plant matter;
(iii) calculating values of actual water concentration in said forced-air entering the solid plant matter with said inlet forced-air temperature value and exiting the solid plant matter with said outlet forced-air temperature value, from said values of maximum water pressure capable of entering and exiting the solid plant matter and from said inlet and said outlet forced-air humidity values;
(iv) determining an implementing status of the method for determining the moisture content and uniformity of the solid plant matter during the on-line drying or cooling forced-air treatment; and
(v) calculating said moisture content value of the solid plant matter from said values of said actual water concentration in said forced-air entering and exiting the solid plant matter and from said forced-air flow rate values.

57. The method of claim 56, whereby the step of obtaining said values of said maximum water partial pressure includes evaluating a function relating said saturation pressure of water in air to temperature of said air at said inlet forced-air temperature value and at said outlet forced-air temperature value.

58. The method of claim 56, whereby the step of obtaining said values of said maximum water partial pressure includes identifying and selecting said values of said maximum water partial pressure at said inlet forced-air temperature value and at said outlet forced-air temperature value from a look-up-table featuring values of said saturation pressure of water in air versus temperature of said air.

59. The method of claim 56, whereby the step of calculating said values of said maximum water concentration includes evaluating a function relating water concentration in air to water partial pressure in said air and temperature of said air at said inlet forced-air temperature value and at said outlet forced-air temperature value.

60. The method of claim 59, whereby said function is a form of the ideal gas law relating said water concentration in said air to molecular weight of said water in said air, said water partial pressure in said air, said temperature of said air, and the universal gas constant, said function is evaluated at said values of said maximum water pressure capable of entering and exiting the solid plant matter.

61. The method of claim 56, whereby the step of calculating said values of said actual water concentration includes evaluating a function relating water concentration in air to water partial pressure in said air, humidity of said air and temperature of said air at said inlet forced-air temperature value and at said outlet forced-air temperature value.

62. The method of claim 61, whereby said function is a form of the ideal gas law relating said water concentration in said air to molecular weight of said water in said air, said water partial pressure in said air, humidity of said air, said temperature of said air, and the universal gas constant, said function is evaluated at said values of said maximum water pressure capable of entering and exiting the solid plant matter, and at said inlet and said outlet forced-air humidity values.

63. The method of claim 56, whereby the step of said determining said implementing status of the method includes calculating and assigning values of quality of said values of said actual water concentration in said forced-air entering and exiting the solid plant matter, at said inlet and said outlet forced-air parametric values, said quality defined as the ratio of said value of said actual water concentration in said forced-air to said value of said maximum water concentration in said forced-air at said forced-air temperature values.

64. The method of claim 63, whereby for said value of said actual water concentration in said forced-air selected from the group consisting of less than and equal to said value of said maximum water concentration in said forced-air, such that said value of said quality of said actual water concentration in said forced-air is selected from the group consisting of less than one and equal to one, then said value of said quality is assigned as a normal implementing status, and there is continuing implementing the method with said step (v).

65. The method of claim 63, whereby for said value of said actual water concentration in said forced-air greater than said value of said maximum water concentration in said forced-air, such that said value of said quality of said actual water concentration in said forced-air is greater than one, then said value of said quality is assigned as an abnormal implementing status, and there is continuing implementing the method with checking the method by at least one selected from the group consisting of an operator of the on-line drying or cooling forced-air treatment and an inspecting device.

66. The method of claim 56, whereby the step of said calculating said moisture content value of the solid plant matter includes evaluating a function of said actual water concentration in said forced-air entering and exiting the solid plant matter and of said outlet forced-air flow rate value.

67. The method of claim 66, whereby said function is of form:

$$W(spm)=k_1[C^{actual}_{in}(water)+[(C^{actual}_{out}(water)-C^{actual}_{in}(water))/(k_2k_3)^f]],$$

wherein said W(spm) is said moisture content value of the solid plant matter, said $C^{actual}_{in}(water)$ is said actual water concentration in said forced-air entering the solid plant matter, said $C^{actual}_{out}(water)$ is said actual water concentration in said forced-air exiting the solid plant matter, said $k_1$, said $k_2$, and said $k_3$, are empirically determined constants, and said f is a function of said outlet forced-air flow rate value, said moisture content value is evaluated as a percent and is proportional to a ratio of mass of said water present in the solid plant matter to mass of the solid plant matter without water.

68. The method of claim 67, whereby said f is a function of form: $FR_{out}(air)$ raised to power of h, equivalent to $[FR_{out}(air)]^h$, where said $FR_{out}(air)$ is said outlet forced-air flow rate value, and said h is an empirically determined constant.

69. The method of claim 43, whereby said uniformity value of the solid plant matter calculated from said at least two said moisture content values is calculated as a function of a parameter selected from the group consisting of time during the on-line forced-air treatment and position of the solid plant matter during the on-line forced-air treatment.

70. The method of claim 43, whereby said calculating said uniformity value of the solid plant matter from said at least two said moisture content values of the solid plant matter further includes generating a profile selected from the group consisting of a position profile of a plurality of said uniformity values at an instant of time during the on-line forced-air treatment and a time profile of said uniformity values for a position of the solid plant matter during the on-line forced-air treatment.

71. The method of claim 43, whereby the step of said calculating said uniformity value of the solid plant matter from said at least two said moisture content values of the solid plant matter is performed by using techniques of statistical analysis.

72. The method of claim 43, whereby said uniformity value of the solid plant matter is evaluated from a plurality of ratios of said moisture content value of the solid plant matter to an average of said at least two said moisture content values of the solid plant matter, using a formula of form:

$U(spm)=[W(spm)]/[W(spm)]_{average}$, where said U(spm) is said uniformity value of the solid plant matter, said [W(spm)] is said moisture content value of the solid plant matter, and said $[W(spm)]_{average}$, is said average of said at least two said moisture content values of the solid plant matter.

73. The method of claim 43, whereby the steps of said sensing and measuring said forced-air operating parameters, said processing said forced-air operating parameters, said calculating said moisture content value of the solid plant matter, and said calculating said uniformity value from said at least two said moisture content values of the solid plant matter, are performed by a central processing unit.

74. The method of claim 43, whereby a plurality of values selected from the group consisting of said moisture content values and said uniformity values is used for achieving high levels of process optimization and control of the drying or cooling forced-air treatment, thereby contributing to optimization and control of an overall manufacturing sequence for producing consumer end products including the solid plant matter as a raw material.

75. A method for non-invasively determining moisture content and uniformity of solid plant matter during on-line drying or cooling forced-air treatment, comprising the steps of:
 (a) sensing and measuring forced-air operating parameters while forced-air enters and exits the solid plant matter, said forced-air operating parameters include temperature, humidity, and flow rate;
 (b) generating raw forced-air parametric values from said sensed and measured forced-air operating parameters, said raw forced-air parametric values include raw forced-air temperature values, raw forced-air humidity values, and raw forced-air flow rate values;
 (c) process correcting said generated forced-air parametric values for forming process corrected forced-air parametric values, said process corrected forced-air parametric values include process corrected forced-air temperature values, process corrected forced-air humidity values, and process corrected forced-air flow rate values, said process correcting accounts for affects of at least one secondary operating parameter on the step of said sensing and measuring said forced-air operating parameters of temperature, humidity, and flow rate;
 (d) calculating a moisture content value of the solid plant matter from said process corrected forced-air parametric values; and
 (e) calculating a uniformity value of the solid plant matter from at least two said moisture content values of the solid plant matter.

76. The method of claim 75, whereby said at least one secondary operating parameter is selected from the group consisting of volumetric bulk transport rate of the solid plant matter, type of the solid plant matter, and, physical characteristics and properties of the solid plant matter.

77. The method of claim 76, whereby said volumetric bulk transport rate of the solid plant matter corresponds to volumetric rate at which the solid plant matter in bulk form is transported by a transport mechanism through a drying or cooling device during the on-line drying or cooling forced-air treatment, said volumetric transport rate is a function of a parameter selected from the group consisting of configuration and volume of said bulk form of the solid plant matter fed onto and situated on said transport mechanism and is a function of linear speed of said transport mechanism moving the solid plant matter through said drying or cooling device.

78. The method of claim 76, whereby said type of the solid plant matter is selected from the group consisting of leaves, beans, seeds, grains, flowers, stems, stalks, and roots, said type of the solid plant matter is in a form selected from the group consisting of raw, processed, loose and web.

79. The method of claim 76, whereby said physical characteristics and properties of the solid plant matter include density of the solid plant matter.

80. A device for non-invasively determining moisture content and uniformity of solid plant matter during on-line drying or cooling forced-air treatment, comprising:
  (a) a solid plant matter inlet, a solid plant matter outlet, and a solid plant matter transport mechanism, for transporting the solid pant matter into and out of the device;
  (b) a forced-air inlet unit, a forced-air outlet unit, and a forced-air supply mechanism, for forcing an air supply into ant out of the device;
  (c) a plurality of forced-air parametric sensors for sensing and measuring forced-air operating parameters of said forced-air entering and exiting the solid plant matter, said forced-air operating parameters include temperature, humidity, and flow rate; and
  (d) a central processing unit for processing said sensed and measured forced-air operating parameters, calculating a moisture content value of the solid plant matter from said sensed and measured forced-air operating parameters, and calculating a uniformity value of the solid plant matter from at least two said moisture content values of the solid plant matter.

81. The device of claim 80, wherein said solid plant matter transport mechanism is a conveyor.

82. The device of claim 80, whereby said forced-air is at conditions corresponding to those selected from the group consisting of laminar flow and turbulent flow, said conditions selected by varying said forced-air operating parameters.

83. The device of claim 80, wherein said forced-air inlet unit features at least one forced-air inlet element for guiding said forced-air into the solid plant matter, and wherein said forced-air outlet unit features at least one forced-air outlet element for guiding said forced-air out of the solid plant matter.

84. The device of claim 80, wherein said forced-air inlet unit is operational in a mode selected from the group consisting of in a fixed position in the device and mobile for moving through the device, and wherein said forced-air outlet unit is operational in a mode selected from the group consisting of in a fixed position in the device and mobile for moving through the device.

85. The device of claim 83, wherein any number of said at least one forced-air inlet element is operational in a mode selected from the group consisting of in a fixed position in the device and mobile for moving through the device, and wherein any number of said at least one forced-air outlet element is operational in a mode selected from the group consisting of in a fixed position in the device and mobile for moving through the device.

86. The device of claim 80, wherein any number of said plurality of forced-air parametric sensors is operational in a mode selected from the group consisting of in a fixed position in the device and mobile for moving through the device.

87. The device of claim 83, wherein said plurality of forced-air parametric sensors includes at least one set of inlet forced-air parametric sensors, and at least one set of outlet forced-air parametric sensors.

88. The device of claim 87, wherein said at least one set of inlet forced-air parametric sensors includes at least one inlet forced-air temperature sensor, at least one inlet forced-air humidity sensor, and at least one inlet forced-air flow rate sensor, and wherein said at least one set of outlet forced-air parametric sensors includes at least one outlet forced-air temperature sensor, at least one outlet forced-air humidity sensor, and at least one outlet forced-air flow rate sensor.

89. The device of claim 87, wherein any number of said at least one set of inlet forced-air parametric sensors is operational in a mode selected from the group consisting of in a fixed position in the device and mobile for moving through the device, and wherein any number of said at least one set of outlet forced-air parametric sensors is operational in a mode selected from the group consisting of in a fixed position in the device and mobile for moving through the device.

90. The device of claim 80, wherein any number of components of the device are automatically controllable and adjustable by said central processing unit and a plurality of control/data links among said components and said central processing unit.

91. The device of claim 87, wherein said forced-air inlet unit and said forced-air outlet unit are electro-mechanically and spatially configured whereby each said forced-air inlet element is associated and axially aligned with a localized said set of said inlet forced-air parametric sensors and whereby each said forced-air outlet element is associated and axially aligned with a localized said set of said outlet forced-air parametric sensors.

92. The device of claim 91, wherein each said association of said forced-air inlet element and said localized set of said inlet forced-air parametric sensors is electro-mechanically paired and axially aligned with a corresponding said association of said forced-air outlet element and said localized set of said outlet forced-air parametric sensors, for obtaining and spatially pairing a set of said sensed and measured inlet forced-air parameters with a corresponding set of said sensed and measured outlet forced-air parameters in a same local vicinity of said forced-air entering and exiting the solid plant matter.

93. The device of claim 80, whereby said temperature, humidity, and flow rate forced-air operating parameters are simultaneously sensed and measured.

94. The device of claim 80, whereby said temperature, humidity, and flow rate forced-air operating parameters are simultaneously processed.

95. The device of claim 80, whereby said sensing and measuring said forced-air operating parameters further includes generating forced-air parametric sensor electrical signals, said forced-air parametric sensor electrical signals include a forced-air temperature sensor electrical signal, a forced-air humidity sensor electrical signal, and a forced-air flow rate sensor electrical signal.

96. The device of claim 95, whereby each said forced-air parametric sensor electrical signal is a function of at least one said forced-air operating parameter.

97. The device of claim 95, whereby said forced-air parametric sensor electrical signals are converted into raw forced-air parametric values, said raw forced-air parametric values include a raw forced-air temperature value, a raw forced-air humidity value, and a raw forced-air flow rate value.

98. The device of claim 97, whereby said raw forced-air parametric values are process corrected for generating process corrected forced-air parametric values for generating process corrected forced-air parametric values, said process corrected forced-air parametric values include a process corrected forced-air temperature value, a process corrected forced-air humidity value, and a process corrected forced-air flow rate value.

99. The device of claim 98, whereby said process correcting of said raw forced-air parametric values accounts for affects of at least one secondary operating parameter on the step of said sensing and measuring said forced-air operating parameters of temperature, humidity, and flow rate.

100. The device of claim 99, whereby said at least one secondary operating parameter is selected from the group consisting of volumetric bulk transport rate of the solid plant matter, type of the solid plant matter, and, physical characteristics and properties of the solid plant matter.

101. The device of claim 100, whereby said volumetric bulk transport rate of the solid plant matter corresponds to volumetric rate at which the solid plant matter in bulk form is transported by said solid plant matter transport mechanism through the drying or cooling device during the on-line drying or cooling forced-air treatment, said volumetric transport rate is a function of a parameter selected from the group consisting of configuration and volume of said bulk form of the solid plant matter fed onto and situated on said solid plant matter transport mechanism and is a function of linear speed of said solid plant matter transport mechanism moving the solid plant matter through the drying or cooling device.

102. The device of claim 100, whereby said type of the solid plant matter is selected from the group consisting of leaves, beans, seeds, grains, flowers, stems, stalks, and roots, said type of the solid plant matter is in a form selected from the group consisting of raw, processed, loose and web.

103. The device of claim 100, whereby said physical characteristics and properties of the solid plant matter include density of the solid plant matter.

104. The device of claim 80, whereby said moisture content value of the solid plant matter is calculated as a function of a parameter selected from the group consisting of time during the on-line forced-air treatment and position of the solid plant matter in the device during the on-line forced-air treatment.

105. The device of claim 80, whereby said calculating said moisture content value of the solid plant matter further includes generating a profile selected from the group consisting of a position profile of a plurality of said moisture content values at an instant of time during the on-line forced-air treatment and a time profile of said moisture content values for a position of the solid plant matter in the device during the on-line forced-air treatment.

106. The device of claim 80, whereby said central processing unit calculates said moisture content of the solid plant matter from said sensed and measured forced-air operating parameters according to the steps of:

(i) obtaining values of maximum water partial pressure corresponding to saturation pressure of water in said forced-air capable of entering the solid plant matter with an inlet forced-air temperature value and exiting the solid plant matter with an outlet forced-air temperature value;

(ii) calculating values of maximum water concentration corresponding to saturation concentration of water in said forced-air capable of entering the solid plant matter with said inlet forced-air temperature value and exiting the solid plant matter with said outlet forced air temper value, from said values of maximum water pressure capable of entering and exiting the solid plant matter;

(iii) calculating values of actual water concentration in said forced-air entering the solid plant matter with said inlet forced-air temperature value and an inlet forced-air humidity value and exiting the solid plant matter with said outlet forced-air temperate value and an outlet forced-air humidity value, from said values of maximum water pressure capable of entering and exiting the solid plant matter;

(iv) determining an implementing status of the device used for determining the moisture content and uniformity of the solid plant matter during the on-line drying or cooling forced-air treatment; and (v) calculating said moisture content value of the solid plant matter from said values of said actual water concentration in said forced-air entering and exiting the solid plant matter and from said forced-air flow rate values.

107. The device of claim 106, whereby said central processing unit obtains said values of said maximum water partial pressure by evaluating a function relating said saturation pressure of water in air to temperature of said air at said inlet forced-air temperature value and at said outlet forced-air temperature value.

108. The device of claim 106, whereby said central processing unit obtains said values of said maximum water partial pressure includes identifying and selecting said values of said maximum water partial pressure at said inlet forced-air temperature value and at said outlet forced-air temperature value from a look-up table featuring values of said saturation pressure of water in air versus temperature of said air.

109. The device of claim 106, whereby said central processing unit calculates said values of said maximum water concentration by evaluating a function relating water concentration in air to water partial pressure in said air and temperature of said air at said inlet forced-air temperature value and at said outlet forced-air temperature value.

110. The device of claim 109, whereby said function is a form of the ideal gas law relating said water concentration in said air to molecular weight of said water in said air, said water partial pressure in said air, said temperature of said air, and the universal gas constant, said function is evaluated at said values of said maximum water pressure capable of entering and exiting the solid plant matter.

111. The device of claim 106, whereby said central processing unit calculates said values of said actual water concentration by evaluating a function relating water concentration in air to water partial pressure in said air, humidity of said air and temperature of said air at said inlet forced-air temperature value and at said outlet forced-air temperature value.

112. The device of claim 111, whereby said function is a form of the ideal gas law relating said water concentration in said air to molecular weight of said water in said air, said water partial pressure in said air, humidity of said air, said temperature of said air, and the universal gas constant, said function is evaluated at said values of said maximum water pressure capable of entering and exiting the solid plant matter, and at said inlet and said outlet forced-air humidity values.

113. The device of claim 106, whereby said central processing unit determines said implementing status of the device by calculating and assigning values of quality of said values of said actual water concentration in said forced-air entering and exiting the solid plant matter, at said inlet and said outlet forced-air parametric values, said quality defined as the ratio of said value of said actual water concentration in said forced-air to said value of said maximum water concentration in said forced-air at said forced-air temperature values.

114. The device of claim 113, whereby for said value of said actual water concentration in said forced-air selected from the group consisting of less than and eval to said value of said maximum water concentration in said forced-air, such that said value of said quality of said actual water concentration in said forced-air is selected from the group consisting of less than one and equal to one, Men said value of said quality is assigned as a normal implementing status, and said central processing unit continues said processing with said step (v).

115. The device of claim 113, whereby for said value of said actual water concentration in said forced-air greater than said value of said maximum water conventration in said forced-air, such that said value of said quality of said actual water concentration in said forced-air is greater than one, then said value of said quality is assigned as an abnormal implementing status, and said central processing unit provides an indication for checking the device by at least one selected from the group consisting of an operator of the on-line drying or cooling forced-air treatment and an inspecting device.

116. The device of claim 106, whereby said central processing unit calculates said moisture content value of the solid plant matter by evaluating a function of said actual water concentration in said forced-air entering and exiting the solid plant matter and of said forced-air flow rate values.

117. The device of claim 116, whereby said function is of form:

$$W(\text{spm}) = k_1[C^{actual}_{in}(\text{water}) + [(C^{actual}_{out}(\text{water}) - C^{actual}_{in}(\text{water}))/(k_2 k_3)^f]],$$

wherein said W(spm) is said moisture content value of the solid plant matter, said $C^{actual}_{in}(\text{water})$ is said actual water concentration in said forced-air entering the solid plant matter, said $C^{actual}_{out}(\text{water})$ is said actual water concentration in said forced-air exiting the solid plant matter, said $k_1$, said $k_2$, and said $k_3$, are empirically determined constants, and said f is a function of said forced-air flow rate values, said moisture content value is evaluated as a percent and is proportional to a ratio of mass of said water present in the solid plant matter to mass of the solid plant matter without water.

118. The device of claim 117, whereby said f is a function of form: $FR_{out}(\text{air})$ raised to power of h, equivalent to $[FR_{out}(\text{air})]^h$, where said $FR_{out}(\text{air})$ is a said forced-air flow rate value of said forced-air exiting the solid plant matter, and said h is an empirically determined constant.

119. The device of claim 80, whereby said uniformity value of the solid plant matter calculated from said at least two said moisture content values is calculated by said central processing unit as a function of a parameter selected from the group consisting of time during the on-line forced-air treatment and position of the solid plant matter in the device during the on-line forced-air treatment.

120. The device of claim 80, whereby said central processing unit calculates said uniformity value of the solid plant matter from said at least two said moisture content values of the solid plant matter by flier generating a profile selected from the group consisting of a position profile of a plurality of said unifomity values at an instant of time during the on-line forced-air treatment and a time profile of said unifomity values for a position of the solid plant matter in the device during the on-line forced-air treatment.

121. The device of claim 80, whereby said central processing unit calculates said uniformity value of the solid plant matter from said at least two said moisture content values of the solid plant matter by using techniques of statistical analysis.

122. The device of claim 80, whereby said uniformity value of the solid plant matter is evaluated by said central processing unit from a plurality of ratios of said moisture content value of the solid plant matter to an average of said at least two said moisture content values of the solid plant matter, using a formula of form:

$U(\text{spm}) = [W(\text{spm})]/[W(\text{spm})]_{average}$, where said U(spm) is said uniformity value of the solid plant matter, said [W(spm)] is said moisture content value of the solid plant matter, and said $[W(\text{spm})]_{average}$, is said average of said at least two said moisture content values of the solid plant matter.

123. The device of claim 80, whereby a plurality of values selected from the group consisting of said moisture content values and said uniformity values is used for achieving high levels of process optimization and control of the drying or cooling forced-air treatment, thereby contributing to optimization and control of an overall manufacturing sequence for producing consumer end products including the solid plant matter as a raw material.

* * * * *

UNITED STATES PATENT AND TRADEMARK OFFICE
CERTIFICATE OF CORRECTION

PATENT NO. : 6,463,794 B1
DATED : October 15, 2002
INVENTOR(S) : Danny S. Moshe et al.

It is certified that error appears in the above-identified patent and that said Letters Patent is hereby corrected as shown below:

Column 13,
Line 23, change "Pms" to -- $P_m$ --
Line 29, change "m" to -- $m$ --; and change "n" to -- $n$ --

Column 15,
Line 54, change "or" to -- of --

Column 16,
Line 19, change "animal" to -- normal --

Column 18,
Line 40, Change "Pm" to -- $P_m$ --

Column 19,
Line 60, change "ate" to -- rate --

Column 29,
Line 24, change "pant" to -- plant --

Column 33,
Line 16, change "eval" to -- equal --
Line 20, change "Men" to -- then --

Column 34,
Line 19, change "flier" to -- further --

Signed and Sealed this

Twenty-fifth Day of February, 2003

JAMES E. ROGAN
*Director of the United States Patent and Trademark Office*